(12) United States Patent
Ogawa et al.

(10) Patent No.: US 9,204,934 B2
(45) Date of Patent: Dec. 8, 2015

(54) MANIPULATOR SYSTEM

(71) Applicant: OLYMPUS CORPORATION, Tokyo (JP)

(72) Inventors: Ryohei Ogawa, Tokyo (JP); Kosuke Kishi, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 0 days.

(21) Appl. No.: 14/147,762

(22) Filed: Jan. 6, 2014

(65) Prior Publication Data

US 2014/0121834 A1     May 1, 2014

Related U.S. Application Data

(63) Continuation of application No. PCT/JP2012/068252, filed on Jul. 11, 2012.

(30) Foreign Application Priority Data

Jul. 15, 2011   (JP) ................................. 2011-156778

(51) Int. Cl.
   *G05B 19/18*    (2006.01)
   *A61B 19/00*    (2006.01)
   *B25J 3/04*     (2006.01)
   (Continued)

(52) U.S. Cl.
   CPC ............... *A61B 19/2203* (2013.01); *B25J 3/00* (2013.01); *B25J 3/04* (2013.01); *B25J 9/1689* (2013.01); *A61B 2019/2223* (2013.01); *A61B 2019/262* (2013.01); *A61B 2019/5227* (2013.01);
   (Continued)

(58) Field of Classification Search
   CPC combination set(s) only.
   See application file for complete search history.

(56) References Cited

U.S. PATENT DOCUMENTS 5,053,975 A * 10/1991 Tsuchihashi et al. ......... 700/264
5,436,542 A    7/1995 Petelin et al.
(Continued)

FOREIGN PATENT DOCUMENTS

JP    01-076695 U    5/1989
JP    03-167698 A    7/1991
(Continued)

OTHER PUBLICATIONS

International Search Report dated Oct. 9, 2012 issued in PCT/JP2012/068252.
(Continued)

*Primary Examiner* — Jonathan L Sample
(74) *Attorney, Agent, or Firm* — Scully, Scott, Murphy & Presser, PC

(57) ABSTRACT

A manipulator system includes a master manipulator configured to send an input command, a slave manipulator configured to operate according to the input command, an image capturing unit configured to acquire an image of an object, a display device placed in front of the operator and configured to display the image acquired by the image capturing unit, a detection device configured to detect the direction of an operator's face of the operator with respect to the display device, and a control unit configured to determine whether the direction of the operator's face is within a predetermined angle with respect to the display device based on the detection result in the detection device, and to shift an operation mode of the slave manipulator between a first control mode and a second control mode in which an operation is limited more than in the first control mode based on a determination result.

14 Claims, 14 Drawing Sheets

(51) Int. Cl.
*B25J 9/16* (2006.01)
*B25J 3/00* (2006.01)

(52) U.S. Cl.
CPC . *A61B2019/5229* (2013.01); *A61B 2019/5297* (2013.01)

(56) References Cited

U.S. PATENT DOCUMENTS

| | | | | |
|---|---|---|---|---|
| 5,876,325 | A * | 3/1999 | Mizuno et al. | 600/102 |
| 6,167,292 | A * | 12/2000 | Badano et al. | 600/407 |
| 6,424,885 | B1 * | 7/2002 | Niemeyer et al. | 700/245 |
| 6,661,571 | B1 * | 12/2003 | Shioda et al. | 359/372 |
| 7,607,440 | B2 * | 10/2009 | Coste-Maniere et al. | 128/898 |
| 8,255,462 | B2 * | 8/2012 | Kondo | 709/205 |
| 8,543,240 | B2 * | 9/2013 | Itkowitz et al. | 700/258 |
| 2002/0128552 | A1 * | 9/2002 | Nowlin et al. | 600/427 |
| 2003/0060927 | A1 * | 3/2003 | Gerbi et al. | 700/245 |
| 2003/0230723 | A1 * | 12/2003 | Garrard et al. | 250/363.1 |
| 2004/0153211 | A1 * | 8/2004 | Kamoto et al. | 700/245 |
| 2005/0033117 | A1 * | 2/2005 | Ozaki et al. | 600/109 |
| 2005/0078854 | A1 * | 4/2005 | Shikano et al. | 382/103 |
| 2005/0222587 | A1 * | 10/2005 | Jinno et al. | 606/130 |
| 2006/0109237 | A1 * | 5/2006 | Morita et al. | 345/156 |
| 2009/0036902 | A1 * | 2/2009 | DiMaio et al. | 606/130 |
| 2009/0097612 | A1 * | 4/2009 | Rauch | 378/19 |
| 2009/0248036 | A1 * | 10/2009 | Hoffman et al. | 606/130 |
| 2009/0268015 | A1 * | 10/2009 | Scott et al. | 348/51 |
| 2011/0083106 | A1 * | 4/2011 | Hamagishi | 715/836 |
| 2011/0118748 | A1 * | 5/2011 | Itkowitz | 606/130 |
| 2011/0276058 | A1 * | 11/2011 | Choi et al. | 606/130 |
| 2012/0071891 | A1 * | 3/2012 | Itkowitz et al. | 606/130 |
| 2012/0071892 | A1 * | 3/2012 | Itkowitz et al. | 606/130 |
| 2014/0081455 | A1 * | 3/2014 | Goldberg et al. | 700/250 |

FOREIGN PATENT DOCUMENTS

| | | |
|---|---|---|
| JP | H05-11713 A | 1/1993 |
| JP | 07-124165 A | 5/1995 |
| JP | H08-280709 A | 10/1996 |
| JP | H09-80323 A | 3/1997 |
| JP | 2000-166873 A | 6/2000 |
| JP | 2003-260685 A | 9/2003 |
| JP | 3482228 B | 12/2003 |
| JP | 2004-261363 A | 9/2004 |
| JP | 2005-219138 A | 8/2005 |
| JP | 2008-262264 A | 10/2008 |
| JP | 2009-45099 A | 3/2009 |
| JP | 2009-244949 A | 10/2009 |
| JP | 2010-097243 A | 4/2010 |
| KR | 10-0998182 B1 | 12/2010 |
| WO | WO 2006/119495 A2 | 11/2006 |

OTHER PUBLICATIONS

Extended Supplementary European Search Report dated Jul. 23, 2015 from related European Application No. 12 81 4731.1.

* cited by examiner

MANIPULATOR SYSTEM

The present invention relates to a manipulator system. This application is a continuation application based on PCT Patent Application No. PCT/JP2012/068252, filed Jul. 11, 2012, claiming priority based on Japanese Patent Application No. 2011-156778 filed on Jul. 15, 2011. The contents of both the PCT Patent Application and the Japanese Patent Application are incorporated herein by reference.

BACKGROUND OF THE INVENTION

1. Field of the Invention
2. Description of Related Art

In the conventional art, as an operation support system, a manipulator system including a master manipulator operated by an operator, and a slave manipulator configured to perform processing based on an operation of the master manipulator is known.

For example, Japanese Unexamined Patent Application, First Publication No. H7-124165 discloses a manipulator control system including a master manipulator (a master arm), a slave manipulator, a stereoscopic scope installed at the slave manipulator, a head mount display (HMD) configured to display an image acquired by the stereoscopic scope, and a control circuit configured to control an operation of the slave manipulator.

The manipulator control system disclosed in Japanese Unexamined Patent Application, First Publication No. H7-124165 detects a line of sight of an operator who performs an operation while wearing the HMD by using a sensor. Then, when the line of sight of the operator is not within a predetermined range, the operation of the slave manipulator is inhibited. According to the manipulator control system, even though the master manipulator is operated when the operator does not see an object to be treated, the slave manipulator does not work.

SUMMARY OF THE INVENTION

According to a first aspect of the present invention, a manipulator system includes a master manipulator configured to send an input command based on manipulation by an operator; a slave manipulator configured to operate in accordance with the input command; an image capturing unit configured to acquire an image of an object; a display device placed in front of the operator and configured to display the image acquired by the image capturing unit; a detection device configured to detect a direction of an operator's face with respect to the display device; and a control unit configured to determine whether the direction of the operator's face is within a predetermined angle with respect to the display device based on a detection result in the detection device, and to shift an operation mode of the slave manipulator between a predetermined first control mode and a second control mode in which an operation is limited more than in the first control mode based on a determination result.

According to a second aspect of the present invention, in the manipulator system according to the first aspect of the present invention, the detection device may include an index unit that is configured to be mountable on the operator to be moved along with the operator's face; and a detection unit positioned with respect to the display device and configured to detect the index unit within a predetermined range. The control unit may operate the slave manipulator in the second control mode when the index unit is not detected within the predetermined range in the detection unit. In addition, the control unit may shift to an input standby mode of an approval signal by the operator to perform a shift from the second control mode to the first control mode when a state in which the index unit is not detected within the predetermined range is changed into a state in which the index unit is detected within the predetermined range. Further, the control unit may perform the shift from the second control mode to the first control mode when the approval signal is input.

According to a third aspect of the present invention, in the manipulator system according to the first aspect of the present invention, the second control mode may be a mode in which the slave manipulator is continuously stopped.

According to a fourth aspect of the present invention, in the manipulator system according to any one of the first to the third aspect of the present invention, the detection device may detect a variation of the direction of the operator's face in a horizontal direction in a state in which the display device is placed in front of the operator. The control unit may shift to the second control mode when the detection device detects that the direction of the operator's face is varied more than the predetermined angle to the horizontal direction.

According to a fifth aspect of the present invention, in the manipulator system according to any one of the first to the fourth aspect of the present invention, the control unit may send a message to prompt the operator to move the operator's face or the display device such that the direction of the operator's face is within a range of the predetermined angle with respect to the display device by using device which is capable of being recognized by the operator, when the control unit determines that the direction of the operator's face deviates from the range of the predetermined angle with respect to the display device.

According to a sixth aspect of the present invention, in the manipulator system according to any one of the first to fourth aspect of the present invention, the control unit may send a message to show a moving direction of the operator's face or the display device such that the direction of the operator's face is within a range of the predetermined angle with respect to the display device by using device that is capable of being recognized by the operator, when the control unit determines that the direction of the operator's face deviates from the range of the predetermined angle with respect to the display device.

According to a seventh aspect of the present invention, in the manipulator system according to the fifth aspect or the sixth aspect of the present invention, the control unit may display the message on the display device.

According to an eighth aspect of the present invention, in the manipulator system according to the first aspect of the present invention, the display device may be provided with a movable mechanism configured to movably support the display device, and the control unit may move the display device by using the movable mechanism such that the direction of the operator's face is within a range of the predetermined angle with respect to the display device, when the control unit determines that the direction of the operator's face deviates from the range of the predetermined angle with respect to the display device.

According to a ninth aspect of the present invention, in the manipulator system according to the first or the second aspect of the present invention, the second control mode may be a mode in which the slave manipulator is operated at an operation speed lower than the first control mode.

According to a tenth aspect of the present invention, in the manipulator system according to any one of the first to the ninth aspect of the present invention, the display device may display two images on the same display surface based on binocular disparity, and a portion of the detection device may be installed at 3D glasses configured to be mountable on the operator and configured to form a stereoscopic image based on the two images.

According to an eleventh aspect of the present invention, in the manipulator system according to the tenth aspect of the present invention, the detection device may detect a distance and a direction of the 3D glasses with respect to the display device, and the control unit may have initial position information showing a range of the distance and direction in which the stereoscopic image is capable of being optimally observed among the distance and the direction. The control unit may shift to the first control mode, based on the initial position information, when the distance and the direction of the 3D glasses detected by the detection device are within the range.

According to a twelfth aspect of the present invention, in the manipulator system according to any one of the second to the eleventh aspect of the present invention, the control unit may perform a shift from the second control mode to the first control mode without input of the approval signal when the direction of the operator's face is within the range of the predetermined angle with respect to the display device within a predetermined time from when the first control mode is shifted to the second control mode.

According to a thirteenth aspect of the present invention, in the manipulator system according to any one of the second to the eleventh aspect of the present invention, the control unit may perform a shift from the second control mode to the first control mode without input of the approval signal when the direction of the operator's face is within the range of the predetermined angle with respect to the display device while an operation amount of the master manipulator from when the shift from the first control mode to the second control mode is performed is within a predetermined operation amount.

According to a fourteenth aspect of the present invention, in the manipulator system according to any one of the second to the thirteenth aspect of the present invention, the index unit may have a predetermined color or a predetermined shape. The detection unit may include an imaging unit configured to acquire an image including the index unit. The control unit may set the predetermined range on the image and recognizes an area having the predetermined color or the predetermined shape in the image as the index unit.

According to a fifteenth aspect of the present invention, in the manipulator system according to any one of the second to the thirteenth aspect of the present invention, the index unit may include a plurality of index elements spaced apart from each other in at least one of a horizontal direction or a vertical direction of the operator wearing the index unit. The detection unit may detect the direction of the index unit based on a result in which positions of the plurality of index elements are detected.

DETAILED DESCRIPTION OF THE INVENTION

Figure 1:
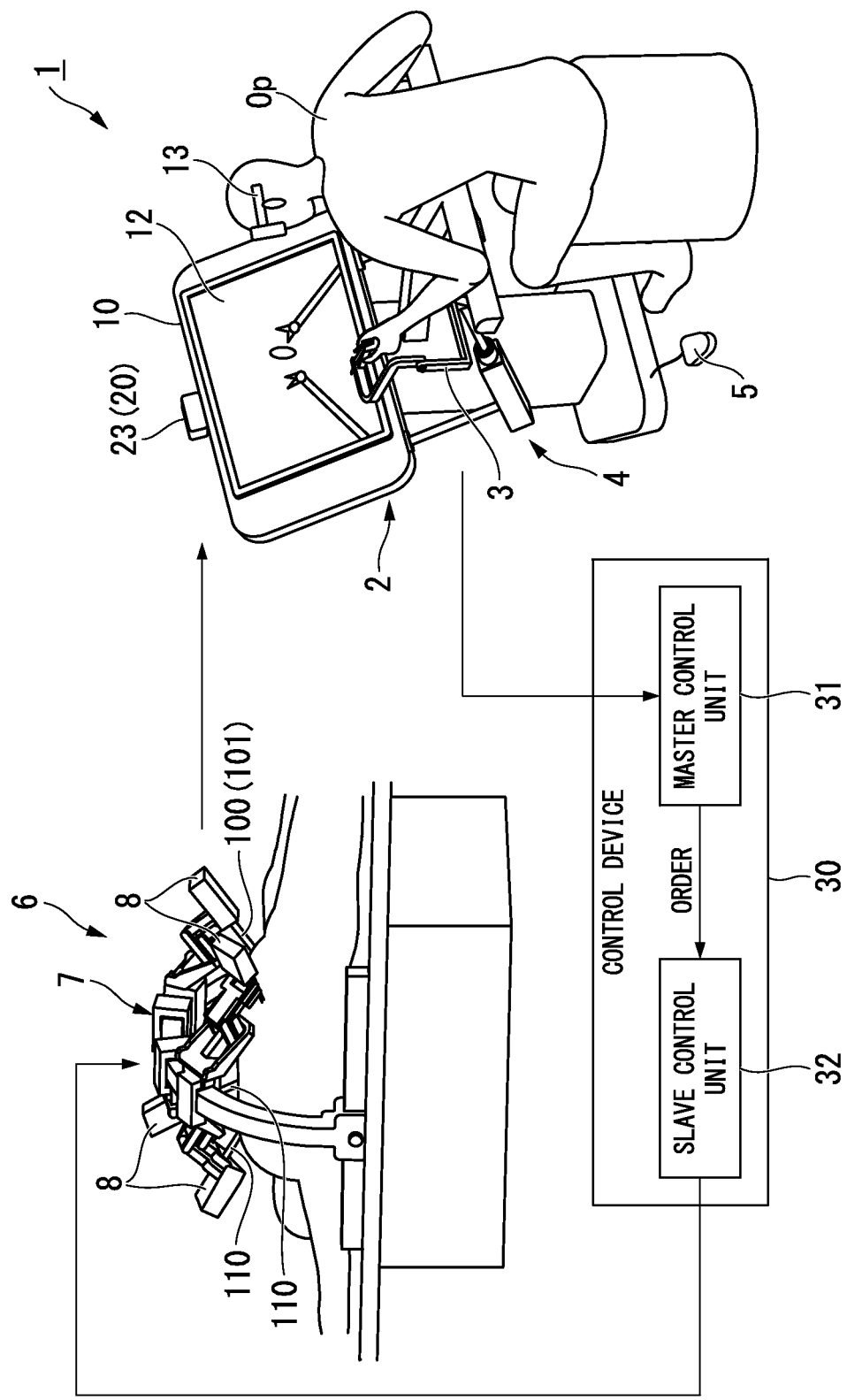
FIG. 1 is an overall view showing a manipulator system according to a first embodiment of the present invention.
Figure 2:
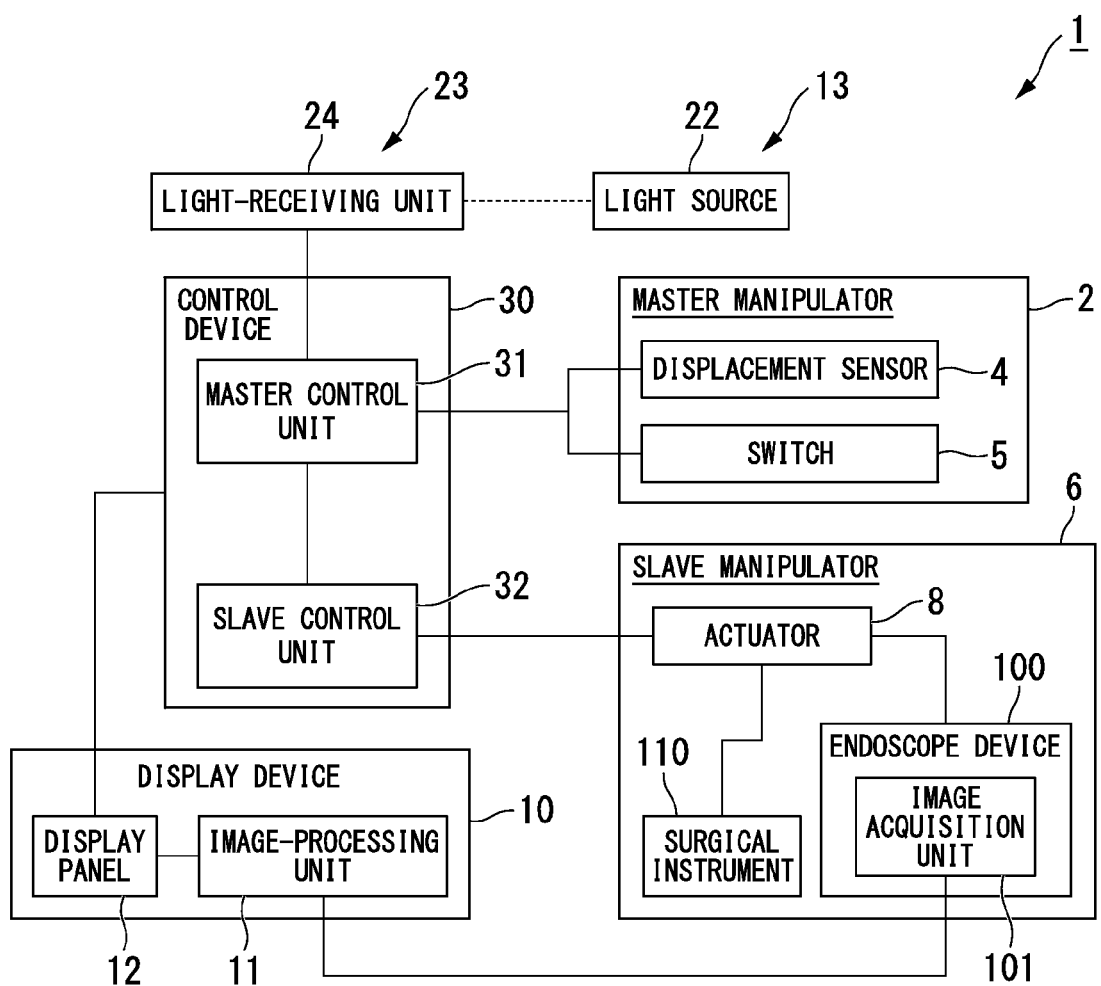
FIG. 2 is a block diagram of the manipulator system according to the first embodiment of the present invention.
Figure 3:
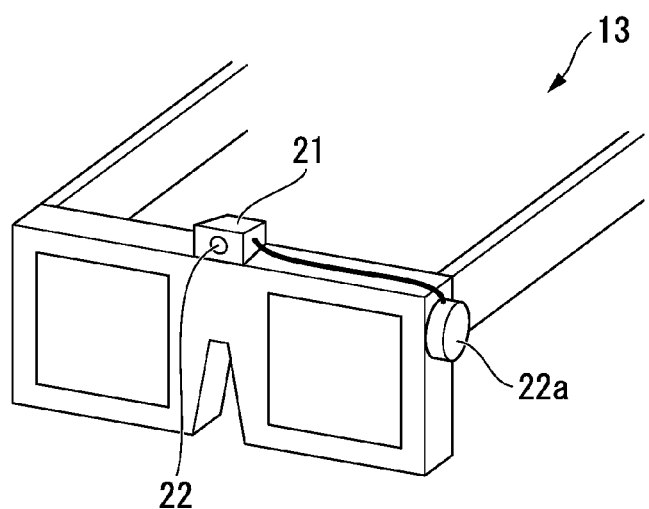
FIG. 3 is a perspective view showing 3D glasses in the manipulator system according to the first embodiment of the present invention.
Figure 4:
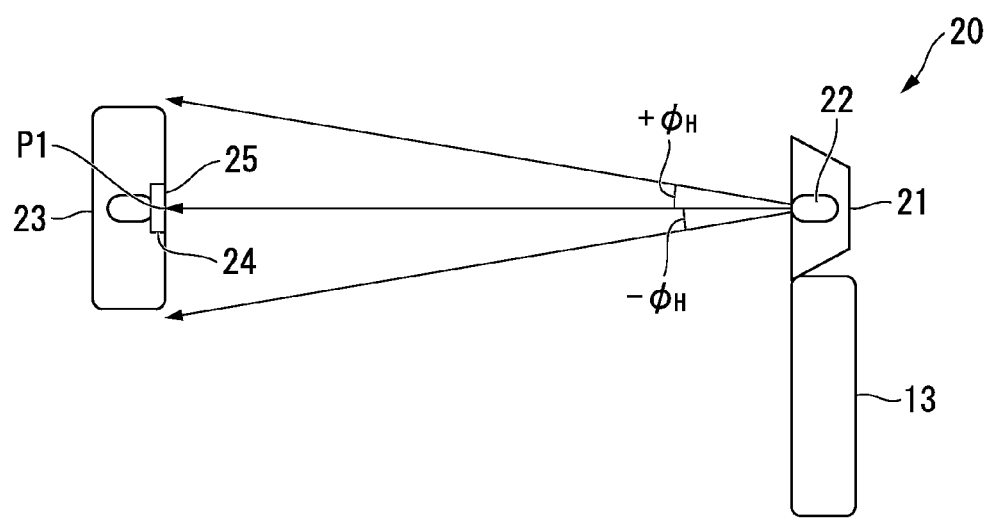
FIG. 4 is a schematic view showing a configuration of a detection device in the manipulator system according to the first embodiment of the present invention.

A manipulator system 1 according to a first embodiment of the present invention will be described. FIG. 1 is an overall view of the manipulator system according to the present embodiment. FIG. 2 is a block diagram of the manipulator system. FIG. 3 is a perspective view showing 3D glasses in the manipulator system. FIG. 4 is a schematic view showing a configuration of a detection device in the manipulator system.

First, the configuration of the manipulator system 1 will be described.

As shown in FIG. 1, the manipulator system 1 includes a master manipulator 2, a slave manipulator 6, a display device 10, a detection device 20, and a control device 30. In addition, the manipulator system 1 according to the present embodiment is a portion of an operation support system used with a surgical instrument 110, an inspection instrument, or the like (not shown).

The master manipulator 2 is provided to transmit movement of an operator Op to the slave manipulator 6. The master manipulator 2 includes a master arm 3 moved by the operator Op, and a switch 5 configured to perform a switch input of the operation mode described below.

The master arm 3 has a multiaxial structure movable within a movable range of the slave manipulator 6 and the surgical instrument 110. In addition, a displacement sensor 4 is attached to the master arm 3. The displacement sensor 4 is configured to send displacement of a position and direction of the master arm 3 as an electrical signal. The electrical signal sent by the displacement sensor 4 is an input command, which is output to the control device 30 and operates the slave manipulator 6. In this way, the master manipulator 2 receives manipulation by the operator Op and sends the input command based on the manipulation by the operator Op.

The switch 5 is a switch in which timing that can be input by a master control unit 31 described below is defined. The switch 5 is arranged on a floor surface near the master manipulator 2. The switch 5 is pushed to output a predetermined return signal to the control device 30.

The slave manipulator 6 includes slave arms 7 and actuators 8. An endoscope device 100 and the surgical instrument 110 are attached to the slave arms 7, respectively. The actuators 8 moves the endoscope device 100, the surgical instrument 110, and the slave arm 7, respectively. The actuators 8 moves the endoscope device 100, the surgical instrument 110, and the slave arm 7 according to any drive signal (described below) output from the control device 30.

The endoscope device 100 installed at the slave manipulator 6 has an image capturing unit 101, and is electrically connected to the display device 10. The image capturing unit 101 acquires an image of an object. The object acquired by the image capturing unit 101 is not particularly limited. For example, the image capturing unit 101 can acquire an image of an object to be treated as an object which is treated by using the endoscope device 100 as an object. In the present embodiment, the image capturing unit 101 acquires two stereoscopic images and outputs the images to the display device 10 as an electrical signal.

The surgical instrument 110 provided at the slave manipulator 6 is provided to perform processing with respect to the object to be treated within a field of vision of the image capturing unit 101. A kind of the surgical instrument 110 is not particularly limited, and a well-known surgical instrument can be appropriately applied according to details of treatment. In addition, the surgical instrument 110 is not limited to the surgical instrument attachable to the slave manipulator 6. For example, the surgical instrument 110 may be a surgical instrument cooperating with the slave manipulator 6.

As shown in FIGS. 1 and 2, the display device 10 is attached to the master manipulator 2, and is placed in front of the operator Op. The display device 10 includes an image processing unit 11 and a display panel 12. The image processing unit 11 is electrically connected to the image capturing unit 101 of the endoscope device 100. The display panel 12 is electrically connected to the image processing unit 11.

The image processing unit 11 generates a stereoscopically visible image by a well-known device on the basis of the electrical signal of the image output from the image capturing unit 101 and outputs the image to the display panel 12.

As the display panel 12, for example, a liquid crystal panel, an organic EL panel, or the like, may be employed. The display panel 12 is configured to display two images having a deviation corresponding to binocular disparity on the same display surface.

As a display method of a stereoscopic image in the display device 10, for example, an image output method of alternately displaying two screens for a right eye and a left eye, or an image output method of displaying two polarized screens for a right eye and a left eye on the same display surface may be provided. The display method of the stereoscopic image in the display device 10 is not limited to these methods as long as the method is a well-known 3D display method.

For example, in the present embodiment, the display device 10 includes 3D glasses 13 that can be worn by the operator Op in order to configure a stereoscopic image based on the two images.

The 3D glasses 13 have a polarizing plate, a liquid crystal shutter, or the like, in order to divide the two images acquired by the image capturing unit 101 to left and right eyes, respectively, to correspond to the display method of each image displayed on the display panel 12. The 3D glasses 13 may be appropriately selected from polarizing glasses, shutter-type glasses, etc. according to the image output method of the display device 10.

In this case, when the operator Op looks at the image displayed on the display device 10, the operator Op wears the 3D glasses 13 and looks at the image via the polarizing plate or the liquid crystal shutter of the 3D glasses 13. For this reason, when the manipulator system 1 is used, the 3D glasses 13 move integrally with the face of the operator Op. In the present embodiment, an index unit 21 (described below), which is a portion of the detection device 20, is installed on the 3D glasses 13.

As shown in FIGS. 3 and 4, the detection device 20 includes the index unit 21 installed at the 3D glasses 13, and a detection unit 23 installed at the display panel 12.

The index unit 21 is fixed to the 3D glasses 13, and includes a light source 22 and a power supply unit 22a. The light source 22 emits a predetermined wavelength of light within a range of a predetermined vertical irradiation angle and horizontal irradiation angle. The power supply unit 22a supplies power to the light source 22. In the present embodiment, a light-emitting diode (LED) is employed as the light source 22, and a lithium polymer battery is employed as the power supply unit 22a.

The detection unit 23 has a light receiving unit 24 configured to receive a light emitted from the light source 22, and is electrically connected to the master control unit 31 described below.

The light-receiving unit 24 has a light receiving surface 25 positioned with respect to the display device 10. A direction of the light receiving surface 25 is determined in consideration of a relation between directions of an operator's face and the display panel 12 when the operator Op looks at a predetermined reference position P1 (see FIG. 5) of the display panel 12, and a positional relation between the operator Op and the display panel 12 in which a stereoscopic image is suitably configured by the image displayed on the display panel 12.

The light receiving unit 24 is configured to detect the index unit 21 installed at the 3D glasses 13 within a range at which the operator Op is present in a state in which the operator Op manipulates the master manipulator 2.

Figure 5:
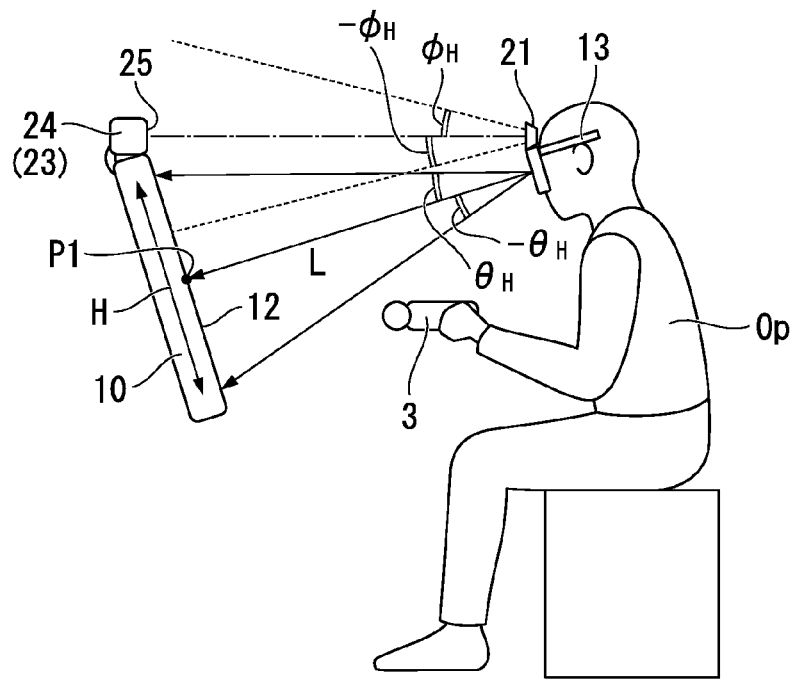
FIG. 5 is a schematic view for explaining a vertical irradiation angle of a light source in the detection device according to the first embodiment of the present invention.
Figure 6:
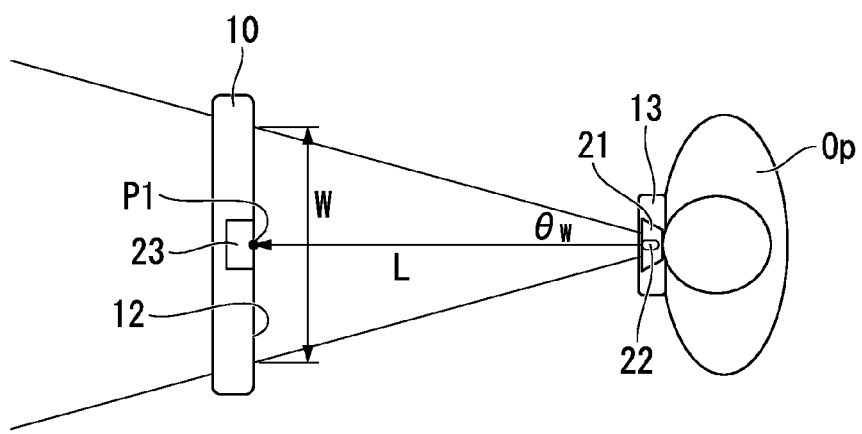
FIG. 6 is a schematic view for explaining a horizontal irradiation angle of the light source in the detection device according to the first embodiment of the present invention.

A configuration of the detection device 20 will be described in detail. FIG. 5 is a schematic view for explaining a vertical irradiation angle of the light source in the detection device. FIG. 6 is a schematic view for explaining a horizontal irradiation angle of the light source in the detection device.

As shown in FIGS. 4 and 5, in the index unit 21, an optical axis of the light source 22 is arranged such that light from the light source 22 arrives at the light-receiving surface 25 in a state in which the operator Op wears the 3D glasses 13 and looks at a predetermined reference position P1 on the display panel 12. In the present embodiment, the reference position P1 is set at a center of the display panel 12.

Here, with reference to 0 degree of a direction of a line of sight when the operator Op looks at the reference position P1, an angle of elevation and an angle of depression are represented as a plus in an upward direction thereof and a minus in a downward direction thereof. Then, a vertical irradiation angle of the light source 22 is determined with reference to a magnitude of the angle of elevation when the operator Op looks up at the uppermost end of the display panel 12 and a magnitude of the angle of depression when the operator Op looks down at the lowermost end of the display panel 12. In the present embodiment, the reference position P1 is a center of the display panel 12. In addition, in the present embodiment, the direction of the face of the operator Op (the operator's face) when the operator Op looks at the reference position P1 is configured to be perpendicular to a direction of the display panel 12. For this reason, absolute values of the sizes of the angle of elevation and the angle of depression are the same.

The direction of the face of the operator Op may be perpendicular to the direction of the display panel 12 such that the operator Op can easily looks at a stereoscopic display displayed on the display panel 12. However, since limitation of disposition may occur according to a place at which the display panel is used, the above configuration is not limited to the perpendicular relation. In this case, the absolute values of the magnitude of the angle of elevation and the magnitude of the angle of depression are different according to initial disposition of the operator Op and the display panel 12.

For example, as shown in FIG. 5 and the following Equation 1, an angle of elevation $\theta_H$ is obtained on the basis of a specific upward/downward dimension H and an optimal distance L to the display panel 12. In addition, the upward/downward dimension H is a length obtained by measuring a length in an upward/downward direction along a surface of the display panel 12 when the display panel 12 is in an installation state. Further, the optimal distance L is a distance within a range in which an image is recognized as the stereoscopic image when a person looks at the image displayed on the display panel 12 via the 3D glasses.

$$\theta_H = \tan^{-1}(H/2L) \quad \text{(Equation 1)}$$

Based on the angle of elevation $\theta_H$ and the angle of depression $-\theta_H$, a horizontal direction (an optical axis center direction) in a state in which the operator Op wears the 3D glasses 13 and looks at the reference position P1 is set as 0 degrees. Then, the vertical irradiation angle of the light source 22 is set within a range from the angle of elevation $\phi_H$ to the angle of depression $-\phi_H$ such that the magnitude of the absolute value is $\theta_H$ or less.

It is known that many people move only their line of sight to look in upward/downward directions, without moving their heads. For this reason, the vertical irradiation angle of the light source 22 may be an angle within a range substantially narrower than the angle of elevation $\theta_H$ and the angle of depression $-\theta_H$.

In addition, a foot switch may be employed as the switch 5 of the master manipulator 2, and other switches may be arranged on a floor surface. In this case, in consideration of the case in which the operator Op faces downward during manipulation, the vertical irradiation angle may be set within a range having a wide upward direction. That is, in this case, since it is not a case that the operator Op to intentionally avoid his or her line of sight from the display panel 12, the setting is varied such that light arrives at a light receiving surface like a state in which the operator Op looks at the display panel 12.

As shown in FIG. 6, in the index unit 21, the horizontal irradiation angle of the light source 22 is set through the same method as the setting method of the vertical irradiation angle. That is, in the index unit 21, with reference to an angle $\theta_W$ obtained by the following Equation 2 on the basis of the width dimension W and the optimal distance L, which are specific dimensions to the display panel 12, the horizontal irradiation angle of the light source 22 is set within a range such that the absolute value is the angle $\theta_W$ or less. In addition, the width dimension W is a length obtained by measuring a length in a horizontal direction of an irradiation range when the display panel 12 is installed, along the surface of the display panel 12.

$$\theta_W = \tan^{-1}(W/2L) \quad \text{(Equation 2)}$$

When the face (the line of sight) of the operator Op faces the display panel 12 of the display device 10, i.e., when the operator Op looks at the display panel 12, the index unit 21 is detected by the detection unit 23. On the other hand, when the operator Op directs his or her face (line of sight) farther outward than an edge of the display panel 12, the index unit 21 is not detected by the detection unit 23. Accordingly, the detection device 20 can detect variation in direction of the face of the operator Op to a vertical direction and a horizontal direction in a state in which the display device 10 is installed.

As shown in FIG. 2, the control device 30 is electrically connected to the master manipulator 2 and the slave manipulator 6 via a signal line, and includes the master control unit 31 and a slave control unit 32.

The master control unit 31 determines whether the direction of the operator's face is within a predetermined angular range with respect to the display device 10 based on the detection result in the detection device 20. The master control unit 31 mutually shifts an operation mode of the slave manipulator 6 between a predetermined first control mode and a second control mode, in which the operation is more restricted than in the first control mode, based on the determination result.

In the present embodiment, the first control mode is an operation mode to operate the slave manipulator 6 such that treatment is performed with respect to the object to be treated. In the first control mode, the operation of the master arm 3 of the master manipulator 2 is transmitted to the slave manipulator 6.

Meanwhile, the second control mode is a mode to stop the operation of the slave manipulator 6 that is not due to the operation of the master arm 3 of the master manipulator 2 and maintain the slave manipulator 6 in a stopped state.

The second control mode is implemented in order to prevent the slave manipulator 6 from moving without relation to the manipulation intended by the operator Op.

In the present embodiment, in the second control mode, all of the input commands sent from the master manipulator 2 are determined as invalid commands in the control device 30. Accordingly, the control device 30 is controlled not to output a command, except for the command by the switch 5, to the slave control unit 32.

In addition, a method of maintaining the slave manipulator 6 in a stopped state is not limited to this method. For example, even in a method of blocking a signal from the master manipulator 2 to the master control unit 31 or a method of blocking a signal from the slave control unit 32 to the slave manipulator 6, the slave manipulator 6 can be maintained in the stopped state.

In the present embodiment, the control device 30 is connected to the display panel 12 of the display device 10. Specifically, the master control unit 31 and the display panel 12 are connected to each other. The control device 30 is configured to display information or a warning related to the operation of the manipulator system 1 on the display panel 12 in characters or symbols.

The slave control unit 32 generates driving signals for operating the slave arm 7, the endoscope device 100, and the surgical instrument 110 based on the input command from the master control unit 31. Then, the slave control unit 32 outputs generated signals to the slave arm 7, the endoscope device 100, and the surgical instrument 110, respectively.

Figure 7:
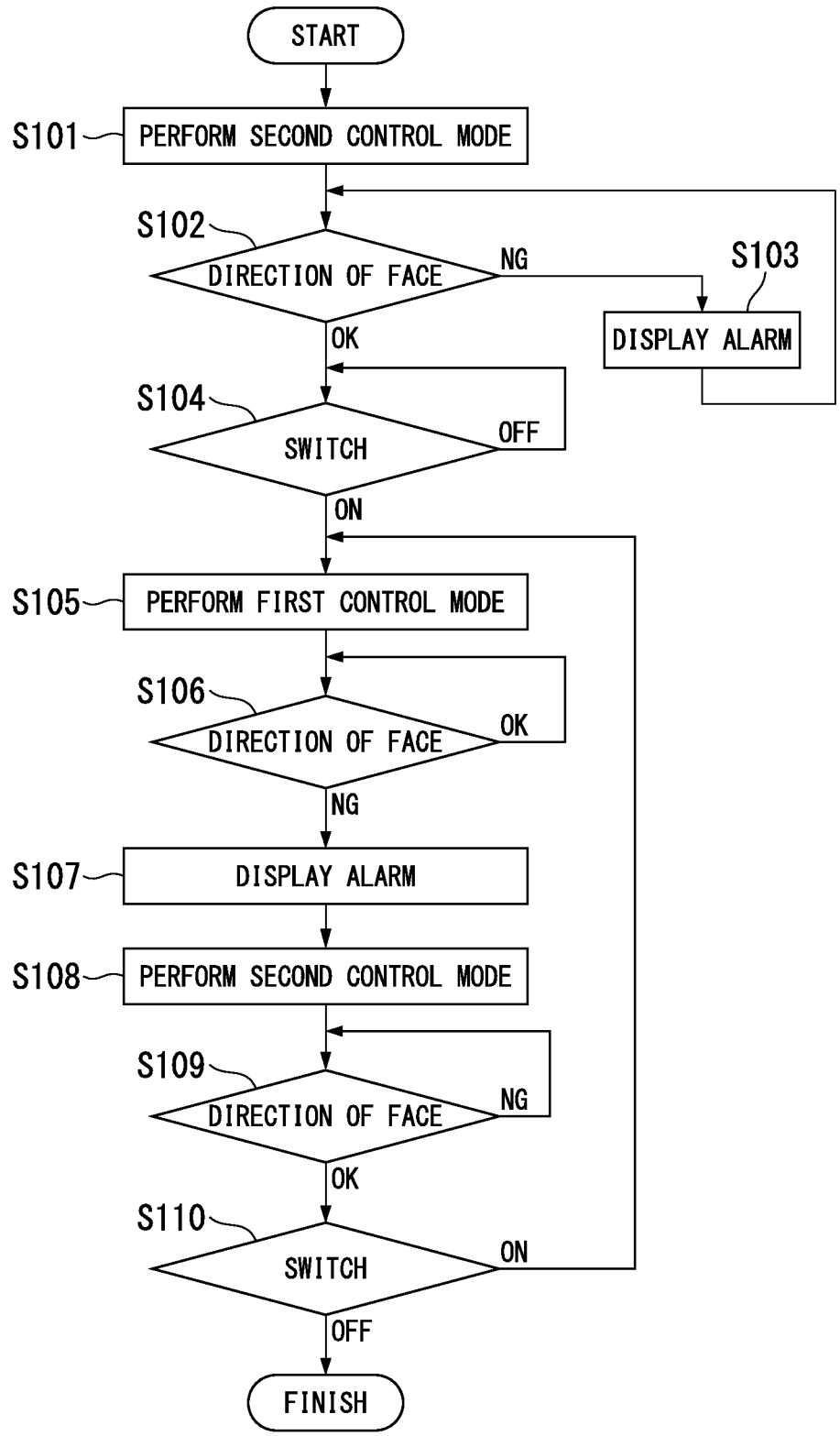
FIG. 7 is a flowchart showing an operation of the manipulator system according to the first embodiment of the present invention.

Next, the initialization before use of the manipulator system 1 and the operation upon use of the manipulator system 1 will be described. FIG. 7 is a flowchart showing an operation of the manipulator system.

As shown in FIG. 7, just after starting the manipulator system 1 (see FIG. 1), an operation mode of the master control unit 31 is set as a second control mode (step S101).

In step S101, even when the operator Op manipulates the master arm 3 of the master manipulator 2, the slave manipulator 6 is not operated. Here, step S101 is finished, and step S102 is started.

Step S102 is a step of dividing processing with reference to the detection result in the detection unit 23.

The manipulator system 1 performs the initialization to instruct the operator Op on a position of the operator Op directed to the display device 10 upon starting use of the manipulator system 1. The initialization is performed to determine disposition of the operator Op and the display device 10 to obtain a positional relation in which the stereoscopic image is appropriately configured.

The operator Op of the manipulator system 1 sits on, for example, a chair, in a state in which his or her face faces the display panel 12 of the display device 10. In addition, the operator Op wears the 3D glasses 13. In order to enable the operator Op to look at the image displayed on the display panel 12 and to recognize the image as the stereoscopic image, the operator Op may be positioned at a position appropriate for the display panel 12. For example, a position or a height of the chair on which the operator Op sits may be appropriately set.

When the light emitted from the light source 22 installed on the 3D glasses 13 arrives at the light-receiving surface 25 of the detection unit 23, the detection unit 23 can detect the index unit 21. On the other hand, when the light emitted from the light source 22 does not arrive at the light receiving surface 25 of the detection unit 23, the detection unit 23 cannot detect the index unit 21. In the manipulator system 1 according to the present embodiment, when the light emitted from the light source 22 installed on the 3D glasses 13 has arrived at the light-receiving surface 25 of the detection unit 23, it is determined that the operator Op normally looks at the stereoscopic image displayed on the display panel 12.

In step S102, the master control unit 31 refers to the detection result in the detection unit 23, and when the index unit 21 is not detected by the detection unit 23, step S103 is started. When the index unit 21 is detected by the detection unit 23, step S104 is started.

Step S103 is a step in which the master control unit 31 sends a message such that the operator Op is prompted to vary the position or direction of the operator Op with respect to the display device 10.

In step S103, the master control unit 31 displays the warning on the display panel 12 of the display device 10. The warning displayed on the display panel 12 is, for example, "Please look in a display direction," "Are you wearing the 3D glasses?" or the like.

Here, step S103 is finished, and step S102 is started.

Step S104 is a step of awaiting input an approval signal by the operator Op to perform a shift from the second control mode to the first control mode.

In step S104, the master control unit 31 displays a message, for example, "Please push the foot switch to start," on the display panel 12 to prompt the operator to press the switch 5.

Step S104 is looped until the switch 5 is pushed, and enters an input standby mode of the approval signal by the operator Op. When the switch 5 is pushed, a return signal from the switch 5 is input to the master control unit 31, step S104 is finished, and step S105 is started.

Step S105 is a step of performing a shift from the second control mode to the first control mode.

In step S105, all of the input commands sent from the master manipulator 2 are determined as valid commands in the master control unit 31.

Here, step S105 is finished, and step S106 is started. After step S105, the input command sent from the master manipulator 2 is output to the slave control unit 32. In this state, when the operator Op manipulates the master arm 3 of the master manipulator 2, the slave control unit 32 generates a driving signal to output the signal to the slave manipulator 6 according to the input command sent from the master manipulator 2. The slave manipulator 6 receives the driving signal output from the slave control unit 32, and operates according to the received driving signal.

Step S106 is a step in which the master control unit 31 detects the direction of the face of the operator Op during the first control mode such that the slave manipulator 6 can be operated.

When the face of the operator Op is largely moved in a horizontal direction or a vertical direction with respect to the display device 10, the 3D glasses 13 worn by the operator Op are also integrally moved with the face of the operator Op. At this time, the light emitted from the light source 22 of the index unit 21 installed on the 3D glasses 13 does not arrive at the light-receiving surface 25 of the detection unit 23. Such an operation occurs, for example, when the operator Op largely moves his/her face in response to a request from a person nearby or rapid change in a state of a patient.

In step S106, similar to step S102, the master control unit 31 determines whether the index unit 21 is detected by the detection unit 23 or not with reference to the detection result in the detection unit 23.

When the index unit 21 is detected by the detection unit 23, step S106 is looped. When the master control unit 31 determines that the index unit 21 is not detected by the detection unit 23, step S106 is finished, and step S107 is started.

In the present embodiment, in step S106, the master control unit 31 determines whether the direction of the face of the operator Op is within a range of an angle when the operator Op appropriately looks at the display panel 12 or not.

Step S107 is a step in which the master control unit 31 displays the warning on the display panel 12 of the display device 10.

In step S107, the master control unit 31 outputs message data such as "Your line of sight has deviated," "Please perform treatment toward the display," or the like, to the display device 10. As these messages are displayed on the display panel 12 of the display device 10, it is possible to prompt the operator Op to look at the display device 10 in a correct direction.

In addition, in step S107, the master control unit 31 may display a message such as "Please adjust a direction of the display" on the display panel 12 of the display device 10. In this case, it is possible to prompt the operator Op to move the display device 10 to a position at which the stereoscopic image is suitably configured at a position of the operator Op in the present state.

Further, in step S107, the master control unit 31 may output a message by sound, instead of displaying the message on the display device 10. Furthermore, the master control unit 31 may have device for issuing a message using device that can be recognized by the operator Op, in addition to written characters (visual information) or sound (audible information). For example, in step S107, a configuration to send a message by tactual information such as vibrations, pressure, or the like, may be considered. Here, step S107 is finished, and step S108 is started.

Step S108 is a step of performing a shift from the first control mode to the second control mode.

In step S108, all of the input commands sent from the master manipulator 2 are determined as invalid commands. Then, these commands are not output to the slave control unit 32. Accordingly, even when the operator Op moves the master arm 3 of the master manipulator 2, the slave manipulator 6 is maintained in the stopped state. Here, step S108 is finished, and step S109 is started.

Step S109 is a step of detecting the direction of the face of the operator Op during the second control mode in which the slave manipulator 6 is in the stopped state.

In step S109, similar to step S102, the master control unit 31 determines whether the index unit 21 is detected by the detection unit 23 or not with reference to the detection result in the detection unit 23. While the index unit 21 is not detected by the detection unit 23, step S109 is looped. When the index unit 21 is detected by the detection unit 23, step S109 is finished, and step S110 is started.

Step S110 is a step of awaiting input of the approval signal by the operator Op to perform a shift from the second control mode to the first control mode.

In step S110, the master control unit 31 displays the message to prompt the operator to push the switch 5 on the display panel 12, and enters an input standby mode to await the input of the approval signal by the operator Op. As the message to prompt that the switch 5 be pressed, for example, "Please push the foot switch to restart," or "Return to home?" may be provided.

When the switch 5 is pushed, as a return signal from the switch 5 is input to the master control unit 31, step S105 is started. When the switch 5 is not pushed, a series of processings of the manipulator system 1 is completed.

In addition, after completion of step S110, processing from step S101 to step S110 may be newly performed.

As described above, in the manipulator system 1 according to the present embodiment, just after starting, the operation of the slave manipulator 6 is in the stopped state. Then, the manipulator system 1 according to the present embodiment is configured such that the slave manipulator 6 can be operated only when the face of the operator Op appropriately faces the display panel 12. In addition, since the direction of the face of the operator Op is detected by whether the light from the light source 22 installed on the 3D glasses 13 arrives at the light-receiving surface 25 or not, the direction of the face of the operator Op can be detected by simple processing. As a result, according to the manipulator system 1 of the present embodiment, the processing is simply performed in comparison with the case in which the line of sight is detected, the entire processing speed is increased, and detection errors are reduced.

In the manipulator system 1 according to the present embodiment, the operator Op concentrates on manipulating an object to be manipulated displayed on the display device 10 installed in front of the operator, and simultaneously, can easily observe the status of the instrument or staff on the periphery through the peripheral field of vision. When the operator Op largely moves his or her line of sight from the display device 10 due to a request from the staff or a sudden change in state of a patient, since awareness of the operator Op deviates from the object to be manipulated, the slave manipulator 6 is stopped for safety. That is, the operator Op can effectively perform the treatment while securing the peripheral field of vision when the operator concentrates on the object to be manipulated. The treatment can be safely stopped when the awareness of the operator Op deviates from the object to be manipulated.

First Modified Example

Figure 8:
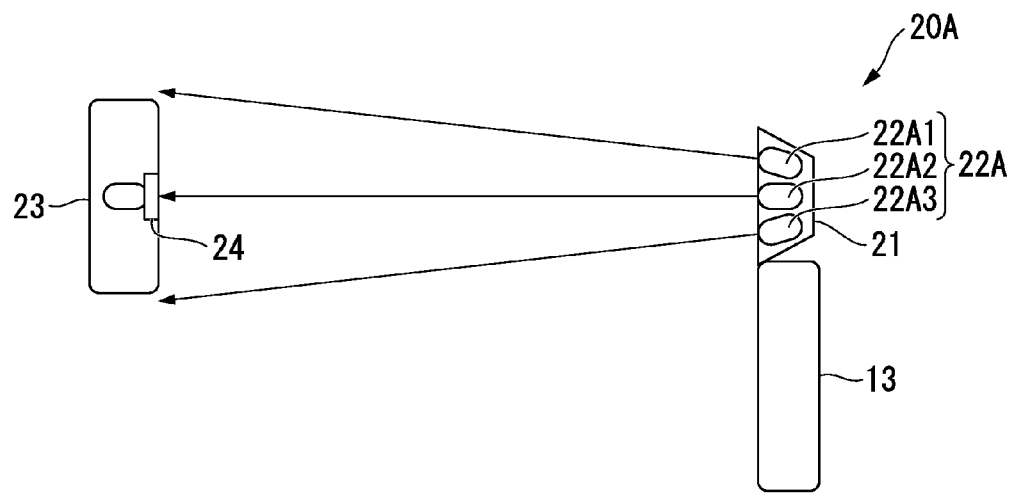
FIG. 8 is a schematic view showing a detection device of a first modified example of the first embodiment of the present invention.

Next, a first modified example of the above-mentioned first embodiment will be described. FIG. 8 is a schematic view showing a detection device of the modified example.

As shown in FIG. 8, the modified example is different from the first embodiment in that the detection device 20 is replaced with a detection device 20A.

The detection device 20A includes a plurality of light sources 22A configured to emit light having high directionality, and the light-receiving unit 24 described in the first embodiment.

In the plurality of light sources 22A, optical axes are directed toward an upper end, a center, and a lower end of the vertical irradiation angle in the index unit 21, respectively.

Even in the configuration shown in the modified example, the same effect as the first embodiment is obtained.

In addition, in the modified example, a light source 22A1, a light source 22A2, and a light source 22A3 having different wavelengths or intensities of the emitted light may be provided as the plurality of light sources 22A, and the light-receiving unit 24 may be configured to discriminate the light source 22A1, 22A2 and 22A3 according to wavelengths. In this case, the detection device 20A can detect whether the face of the operator Op moves to an upward or downward direction of the display device 10.

In addition, as further modified example of the modified example, instead of the light source 22A, the plurality of light sources in which optical axes are directed toward a right end, a center, and a left end of the horizontal irradiation angle in the index unit 21, respectively, may be installed on the detection device 20A.

Second Modified Example

Figure 9:
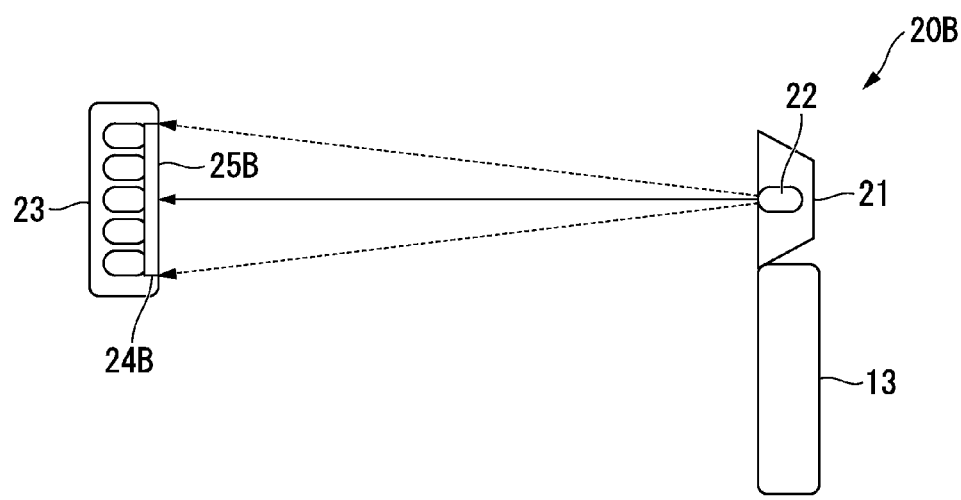
FIG. 9 is a schematic view showing a detection device of a second modified example of the first embodiment of the present invention.

Next, a second modified example of the above-mentioned first embodiment will be described. FIG. 9 is a schematic view showing a detection device of the modified example.

As shown in FIG. 9, the modified example is different from the first embodiment in that the detection device 20 is replaced with a detection device 20B.

In the detection device 20B, instead of the light-receiving unit 24, a light-receiving unit 24B having a light-receiving surface 25B at which a plurality of light-receiving elements are arranged is installed.

In the modified example, as it is detected to which one of the plurality of light-receiving elements the light emitted from the light source 22 is irradiated, a direction to which the light source 22 is moved with respect to the light-receiving unit 24B can be detected.

Third Modified Example

Figure 10:
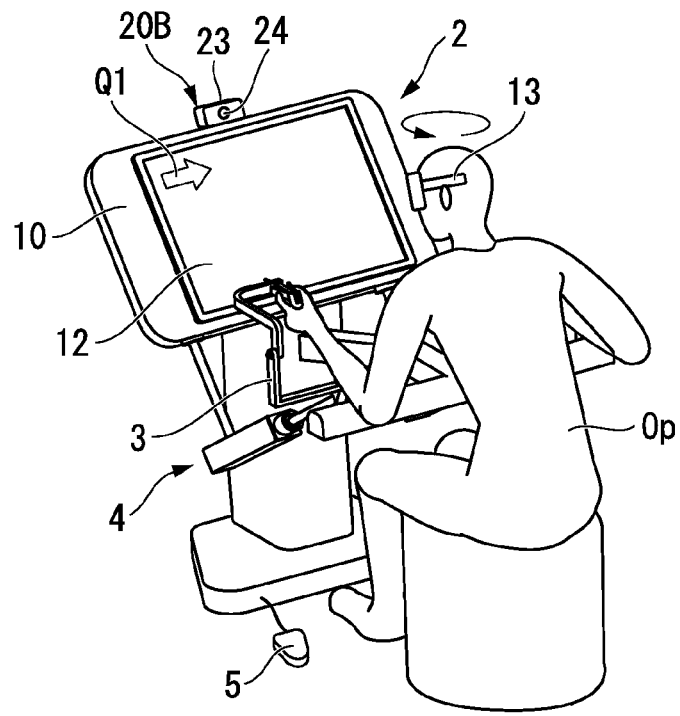
FIG. 10 is a perspective view showing a partial configuration of a manipulator system of a third modified example of the first embodiment of the present invention.

Next, a third modified example of the above-mentioned first embodiment will be described. FIG. 10 is a perspective view showing a partial configuration of a manipulator system of the modified example.

The modified example is different from the first embodiment in that the detection device 20B described in the above-mentioned second modified example is provided, and the master control unit 31 is differently operated from the above-mentioned first embodiment.

In addition, the third modified example is different from the first embodiment in treatment of the master control unit 31 in step S107. That is, when it is determined that the direction of the face of the operator Op does not face the display panel 12 in step S106 of the first embodiment, the master control unit 31 displays arrow symbols (see reference numeral Q1 of FIG. 10) of a direction which is an opposite direction of the light source 22 being moved with respect to the light receiving unit 24 upon determination, and a message such as "Please direct your face toward the display," on the display panel 12, instead of step S107 of the first embodiment.

In the modified example, it is possible for the operator Op to easily understand a preferable direction to turn the face of the operator Op by the arrow symbol.

Fourth Modified Example

Figure 11:
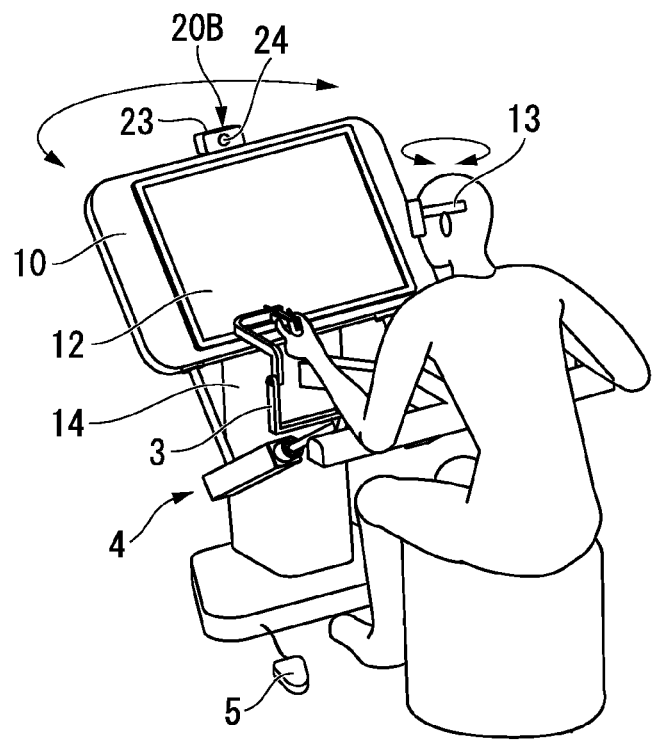
FIG. 11 is perspective view showing a partial configuration of a manipulator system of a fourth modified example of the first embodiment of the present invention.

Next, a fourth modified example of the above-mentioned first embodiment will be described. FIG. 11 is a perspective view showing a partial portion of a manipulator system of the modified example.

As shown in FIG. 11, the modified example is different from the first embodiment in that the detection device 20B described in the above-mentioned second modified example is provided, and a movable mechanism 14 configured to movably support the display panel 12 is installed at the display device 10. In addition, the modified example is different from the first embodiment in that the master control unit 31 is differently operated from the above-mentioned first embodiment.

The movable mechanism 14 includes, for example, a servo-motor, and controls a position and direction in upward/downward rightward/leftward directions of the display panel 12 under control of the master control unit 31.

When it is determined that the direction of the face of the operator Op does not face the display panel 12 in step S106 of the first embodiment, the master control unit 31 moves the display panel 12 in the same direction as the direction in which the light source 22 moves with respect to the light receiving unit 24 upon determination, by the movable mechanism 14, instead of step S107 of the first embodiment.

In the modified example, since the display panel 12 moves according to the direction to which the face of the operator Op is directed, the operator Op can continue an operation in the first control mode.

Fifth Modified Example

Next, a fifth modified example of the above-mentioned first embodiment will be described.

Figure 12:
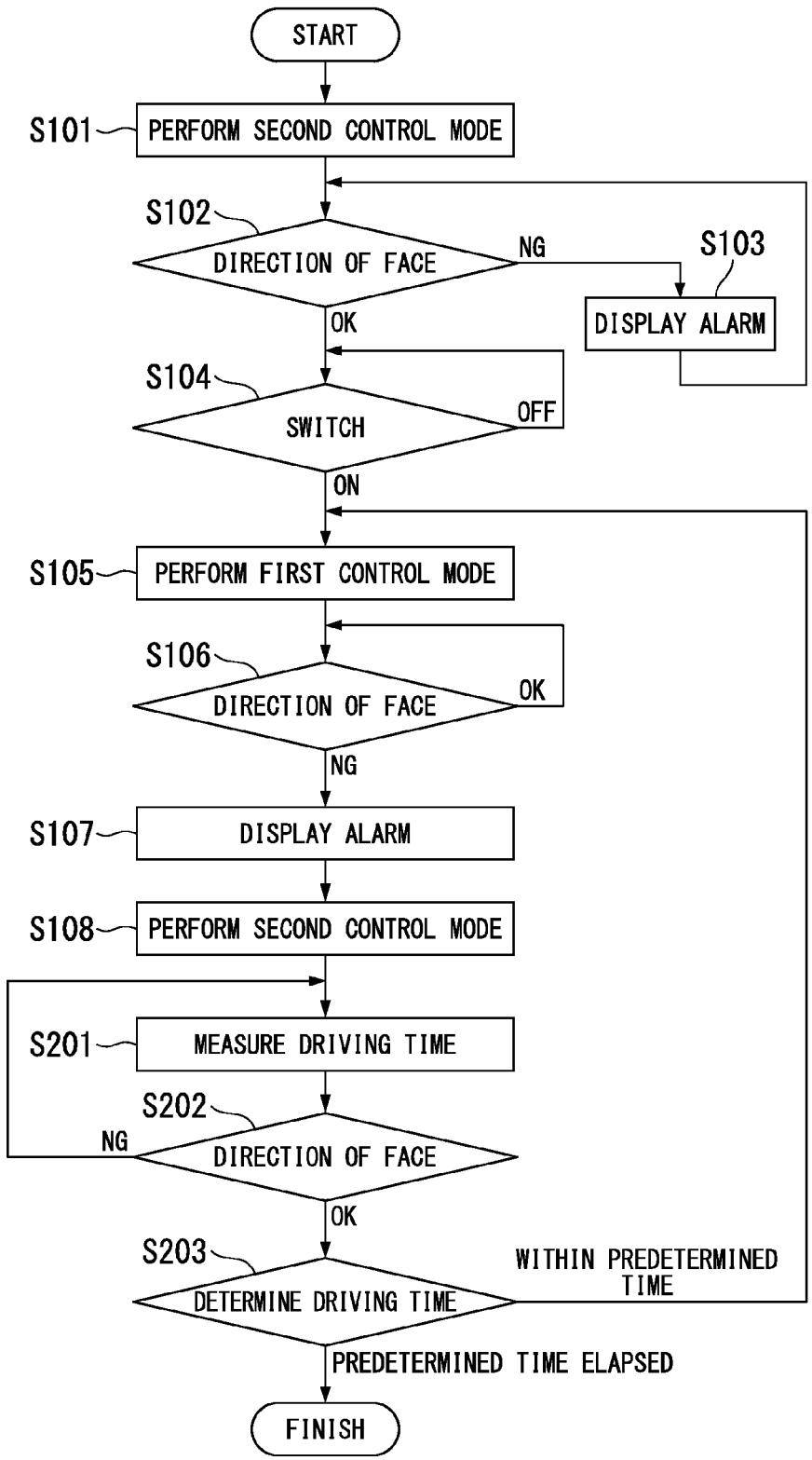
FIG. 12 is a flowchart showing an operation of a manipulator system of a fifth modified example of the first embodiment of the present invention.

The modified example is different from the above-mentioned first embodiment in an operation of the master control unit 31. FIG. 12 is a flowchart showing the operation of the master control unit 31 in the modified example. In FIG. 12, the process which is the same process as those in the above-mentioned first embodiment are assigned the same symbols, and so description thereof will be omitted.

As shown in FIG. 12, after completion of step S108, measurement of an operation time in the second control mode is started (step S201).

In step S201, for example, a timer may be reset to perform a count-up operation at a time to shift to the second control mode, or a countdown timer set to a predetermined time to be described later may be started. Here, step S201 is finished, and step S202 is started.

Step S202 is a step in which the detection unit 23 detects a direction of the face of the operator Op while the slave manipulator 6 is in a stopped state.

In step S202, similar to step S102 of the first embodiment, the master control unit 31 determines whether the index unit 21 is detected by the detection unit 23 or not, with reference to the detection result in the detection unit 23.

When the index unit 21 is not detected by the detection unit 23, step S201 is started again. The master control unit 31 is maintained in the second control mode, and in step S201, the operation time is continuously measured. Until the index unit 21 is detected by the detection unit 23, the operation time is continuously added.

When the index unit 21 is detected by the detection unit 23, step S202 is finished, and step S203 is started.

Step S203 is a step in which the master control unit 31 divides the treatment based on the time measured in step S201.

In step S203, when the measured time is within the predetermined time, step S105 is started, and the master control unit 31 shifts from the second control mode to the first control mode.

In addition, when the measured time exceeds the predetermined time, the manipulator system 1 finishes a series of treatments. Meanwhile, when the manipulator system 1 is continuously used, the treatment from step S101 is performed again. In this case, since the index unit 21 is detected by the detection unit 23 in a state upon completion, the operation is performed to S104, and determination of presence of the input of the approval signal by the switch 5 is performed. After that, the same flow as in the first embodiment is performed.

Further, the predetermined time is appropriately set as a length of time in which a risk is low even when the line of sight deviates from the image in which the object to be treated is displayed.

In the modified example, when the time in which the line of sight of the operator Op deviates from the display panel 12 exceeds the predetermined time, in order to perform a shift to the first control mode, input of the approval signal by the switch 5 is needed. In addition, the master control unit 31 can shift to the first control mode with no need to input the approval signal by the switch 5 when the time in which the line of sight of the operator Op deviates from the display panel 12 is short.

Sixth Modified Example

Next, a sixth modified example of the first embodiment will be described.

Figure 13:
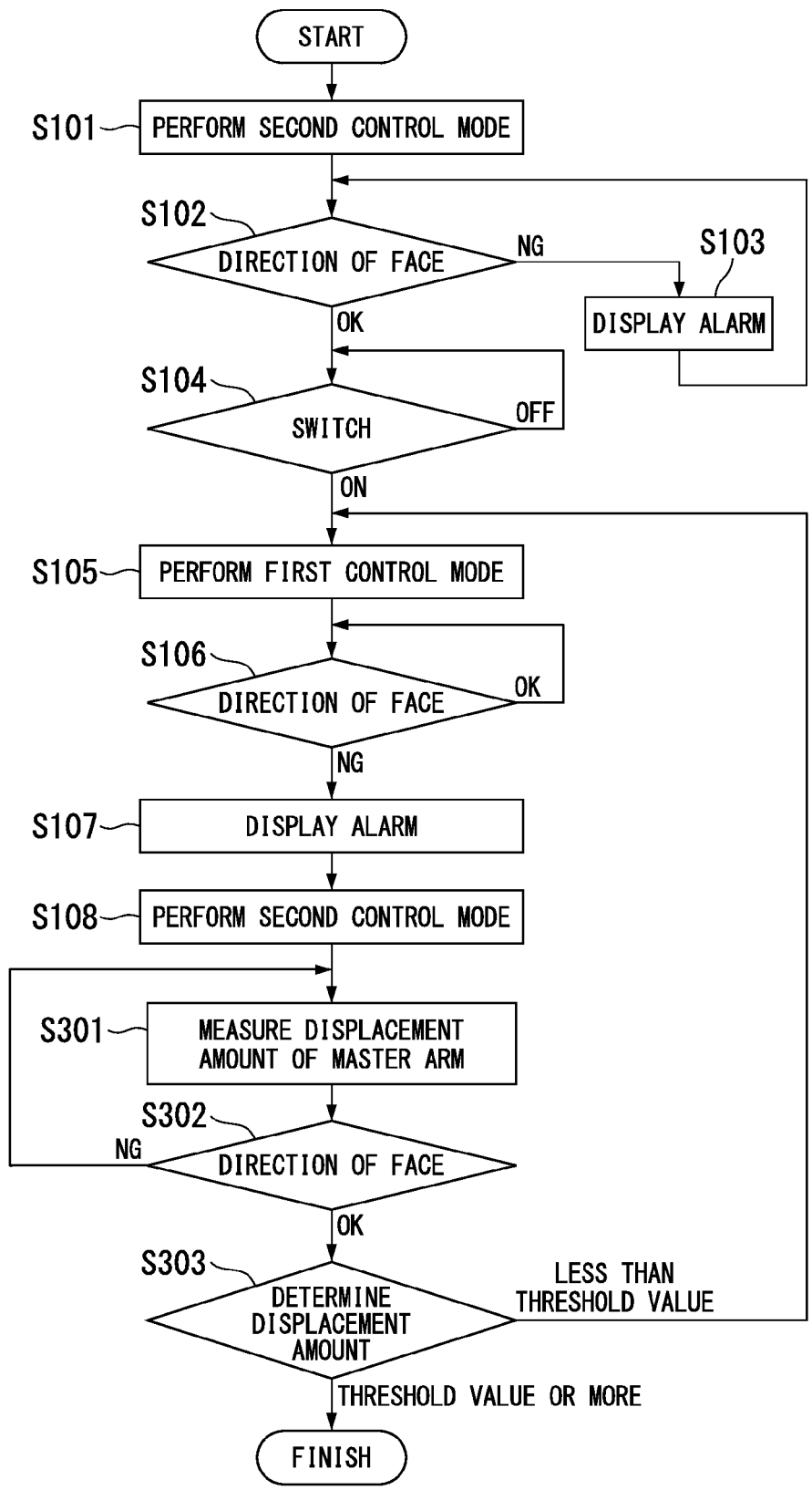
FIG. 13 is a flowchart showing an operation of a manipulator system of a sixth modified example of the first embodiment of the present invention.

The modified example is different from the first embodiment in the operation of the master control unit 31. FIG. 13 is a flowchart showing an operation of the master control unit 31 in this modified example. In FIG. 13, the process which is the same process as those in the above-mentioned first embodiment are assigned the same symbols, and so description thereof will be omitted.

As shown in FIG. 13, in this modified example, after completion of step S108, a displacement of the master arm 3 is measured (step S301). The displacement of the master arm 3 is temporarily stored in the control device 30.

Here, step S301 is finished, and step S302 is started.

Step S302 is, similar to step S202 of the fifth modified example, a step of detecting the direction of the face of the operator Op while the slave manipulator 6 is in the stopped state.

When the index unit 21 is not detected by the detection unit 23, step S301 is started again, and the master control unit 31 is maintained as the second control mode. Then, in step S301, the displacement of the master arm 3 is continuously measured. Until the index unit 21 is detected by the detection unit 23, the displacement is continuously added. In the modified example, the displacement is obtained as a distance moved by adding an absolute value of the detected displacement of the master arm 3. In addition, the displacement of the master arm 3 may be a variation in position from the initial position. Further, the determination may be performed with respect to a variation in orientation of the master arm 3, rather than the position of the master arm 3.

When the index unit 21 is detected by the detection unit 23, step S302 is finished, and step S303 is started.

Step S303 is a step of dividing the treatment based on the displacement of the master arm 3 measured in step S301.

In step S303, when the measured displacement of the master arm 3 is less than a threshold value, step S105 is started, and the master control unit 31 performs a shift from the second control mode to the first control mode. At this time, input of the return signal using the switch 5 is not needed.

In addition, when the measured displacement is the threshold value or more, a series of treatments of the manipulator system 1 are finished.

In the modified example, when the master arm 3 is moved to the threshold value or more after the line of sight of the operator Op deviates from the display panel 12, in order to enable the operation of the slave manipulator 6 again, input of the return signal using the switch 5 is needed.

In addition, even when the line of sight of the operator Op deviates from the display panel 12, if the displacement of the master arm 3 is less than the threshold value, when the line of sight of the operator Op returns to the display panel 12, the slave manipulator 6 can be immediately operated with no necessity to input the return signal using the switch 5.

Seventh Modified Example

Figure 14:
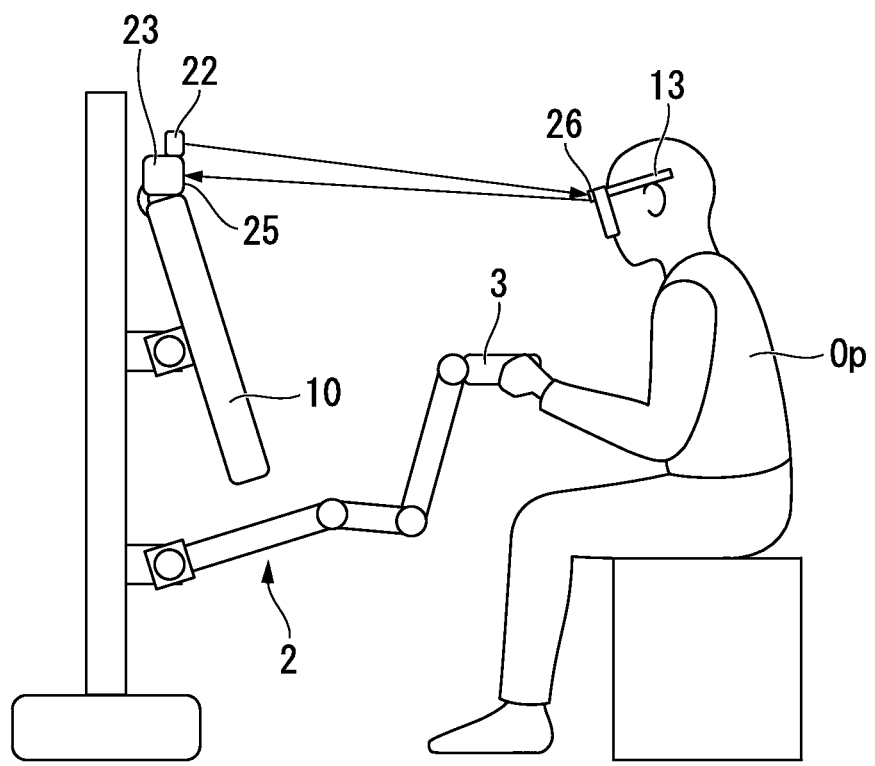
FIG. 14 is a schematic view showing a partial configuration of a manipulator system of a seventh modified example of the first embodiment of the present invention.

Next, a seventh modified example of the above-mentioned first embodiment will be described. FIG. 14 is a schematic view showing a partial configuration of a manipulator system of the modified example.

As shown in FIG. 14, the modified example is different from the first embodiment in that the light source 22 is installed at the detection unit 23 and a reflecting unit 26 configured to reflect the light emitted from the light source 22 is installed at the index unit 21.

In the modified example, when arrival of the light emitted from the light source 22 and reflected by the reflecting unit 26 at the light receiving surface 25 is detected by the detection unit 23, the master control unit 31 determines that the face of the operator Op is appropriately directed to the display panel 12.

Even in the above-mentioned configuration, the same effect as the above-mentioned first embodiment is obtained.

In addition, even in the case of the modified example, since the reflecting unit 26 may not be an electronic part, a separate power supply is not needed for the 3D glasses worn by the operator Op.

Eighth Modified Example

Figure 15:
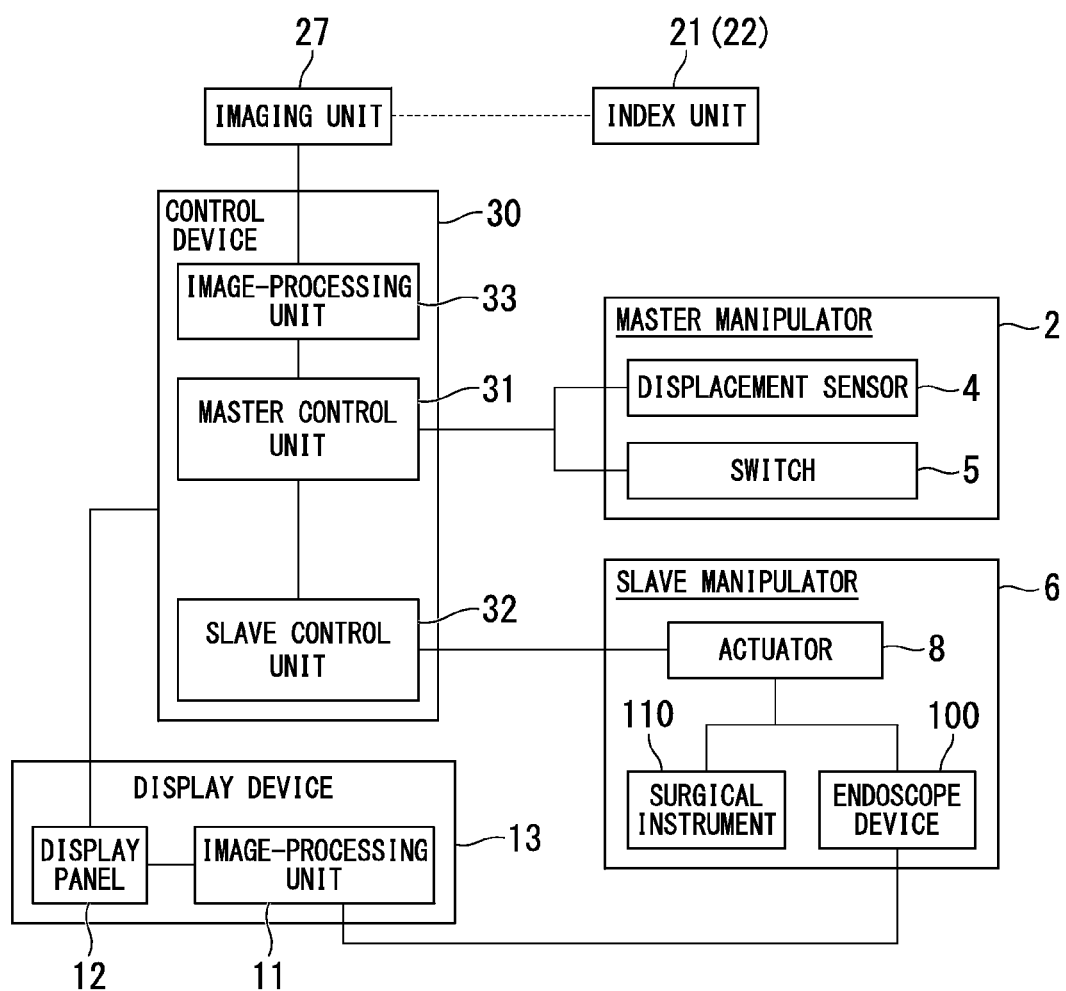
FIG. 15 is a block diagram showing a manipulator system of an eighth modified example of the first embodiment of the present invention.

Next, an eighth modified example of the above-mentioned first embodiment will be described. FIG. 15 is a block diagram showing a manipulator system of the modified example.

As shown in FIG. 15, the modified example is largely different from the first embodiment in that an imaging unit 27 is provided instead of the light receiving unit 24. As the imaging unit 27, a CCD sensor, a CMOS sensor, or the like, may be employed.

In the modified example, the imaging unit 27 receives the light emitted from the light source 22, and obtains an image including a bright section X1 generated by the light from the light source 22 and the other section (a dark section X2) to output the image to the control device 30.

The control device 30 has an image processing unit 33 configured to detect a variation in size of the bright section X1 by conventional edge detection, etc., and calculates a distance between the imaging unit 27 and the index unit 21 based on the size of the bright section X1.

In the case of the modified example, since the distance between the imaging unit 27 and the index unit 21 can be calculated, a distance between the display device 10 and the 3D glasses 13 can be precisely estimated. Accordingly, it is possible to determine whether the distance between the display device 10 and the 3D glasses 13 is near an optimal distance L at which the stereoscopic image can be appropriately configured. Further, in response to the distance between the display device 10 and the 3D glasses 13, a message can be appropriately selected to be displayed on the display panel 12, and it is possible to prompt the operator Op to move to a position at which the stereoscopic image is suitably observed. As the message in this case, for example, "Please approach the display," "Please move away from the display," or the like, may be provided.

Figure 16:
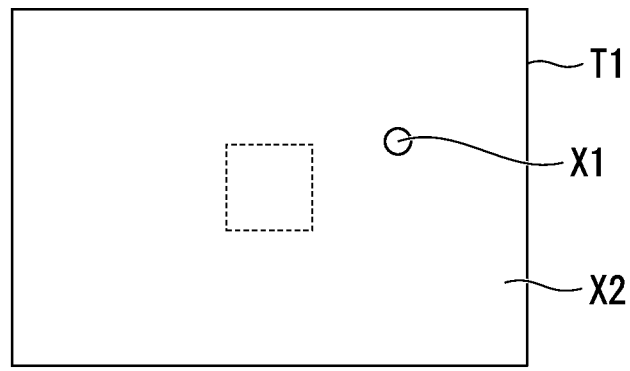
FIG. 16 is a view for explaining an initializing operation in the manipulator system of the eighth modified example of the first embodiment of the present invention.
Figure 17:
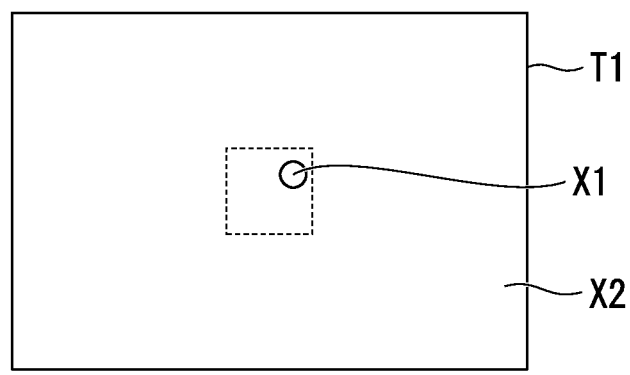
FIG. 17 is a view for explaining the initializing operation in the manipulator system of the eighth modified example of the first embodiment of the present invention.
Figure 18:
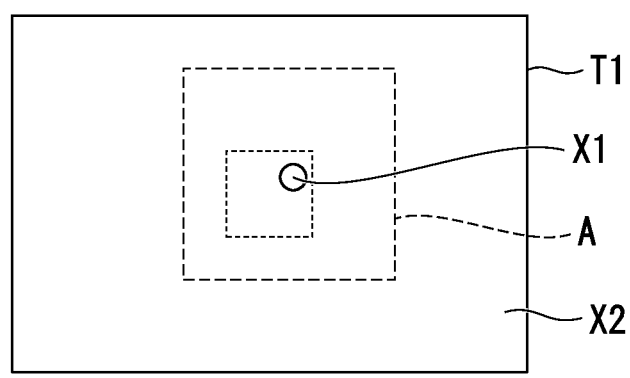
FIG. 18 is a view for explaining the initializing operation in the manipulator system of the eighth modified example of the first embodiment of the present invention.

Next, an initialization method of a positional relation between the imaging unit 27 and the index unit 21 of the manipulator system 1 in the modified example will be described. FIGS. 16 to 18 are views for explaining an initialization operation in the manipulator system of the modified example.

In the modified example, the initialization of the manipulator system 1 is processing to set a rectangular range A based on a position of an edge of the display panel 12 in an imaging region T1 by the imaging unit 27.

First, the operator Op wearing the 3D glasses 13 looks at the reference position P1 of the display panel 12. The reference position P1 of the display panel 12 is, similar to the first embodiment, a center of the display panel 12. Then, the light from the light source 22 installed on the 3D glasses 13 is irradiated to some positions in the imaging region T1 of the imaging unit 27. At this time, the control device 30 displays an image having a mark showing a position of the light from the light source 22 on the image which resembles the imaging region T1 of the imaging unit 27 on the display panel 12. The operator Op adjusts a position and direction of the display panel 12 or the operator Op such that the light from the light source 22 is irradiated to a substantially center of the imaging region T1 with reference to the image displayed on the display panel 12.

Thereafter, the control device 30 set the rectangular range A, a center of which is the bright section X1, in the imaging region T1. A shape and size of the range A are appropriately determined by the shape and size of the display panel 12. Further, the size of the range A is increased as the size of the bright section X1 is reduced, and is reduced as the size of the bright section X1 is increased. This is because, even though a variation in angle of the direction of the face of the operator Op is equal, when the distance between the operator Op and the display device 10 is large, a moving distance of the bright section X1 on the imaging region T1 is increased.

In the case of the modified example, when the bright section X1 is positioned at an outer region of the range A, the control device 30 determines that the line of sight of the operator Op deviates from the display panel 12. In addition, when the bright section X1 is positioned in an inner region of the range A, the control device 30 determines that the operator Op looks at the display panel 12.

Further, when the range A can be set in the imaging region T1 of the imaging unit 27, there is no need to set the reference position P1 of the display panel 12 at a center of the display panel 12. For example, when a plurality of images are displayed on the display panel 12 and the image to be watched carefully is disposed at a position other than the center of the display panel 12, a place at which the image to be watched carefully is disposed may be set as the reference position P1. Even in this case, the initialization can be performed as described above.

In addition, when the range A is to be set in the imaging region T1, if the range A extends outside from the imaging region T1, the control device 30 may display a message representing an intent on the display panel 12 of the display device 10. Accordingly, it is possible to prompt the operator Op to move a position of the operator Op or a position of the display device 10.

Ninth Modified Example

Figure 19:
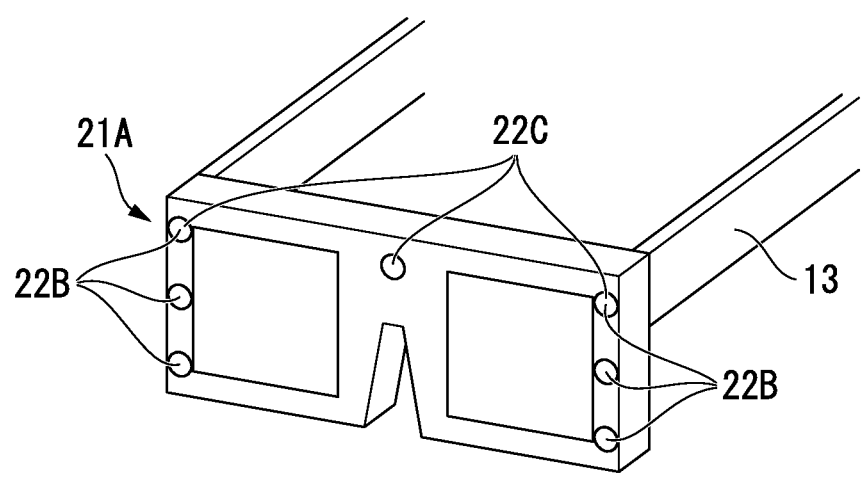
FIG. 19 is a perspective view showing a configuration of 3D glasses in a manipulator system of a ninth modified example of the first embodiment of the present invention.

Next, a ninth modified example of the above-mentioned first embodiment will be described. FIG. 19 is a perspective view showing a configuration of 3D glasses of a manipulator system of the modified example.

As shown in FIG. 19, the modified example is different from the first embodiment in that the imaging unit 27 described in the above-mentioned eighth modified example is provided, and the index unit 21A including a first index element and a second index element is provided instead of the index unit 21. The first index element is constituted by a plurality of light sources 22B spaced apart from each other in a vertical direction. The second index element is constituted by a plurality of light sources 22C spaced apart from each other in a horizontal direction.

In the case of this modified example, all light emitted from the plurality of light sources 22 can be irradiated to the imaging region T1 of the imaging unit 27, and a variation in size of the bright section X1 can be detected by each of the light sources 22. Accordingly, the detection device 20 can detect a distance and a direction of the 3D glasses 13 with respect to the imaging unit 27, i.e., a distance and a direction of the 3D glasses 13 with respect to the display device 10, by the distance calculated on the basis of the sizes of the plurality of the bright sections X1.

When the 3D glasses 13 are inclined with respect to the display panel 12, the stereoscopic image may not be appropriately configured. In the case of the modified example, initial position information representing a range of the distance and direction of the 3D glasses 13 with respect to the display device 10 when the stereoscopic image is suitably configured is stored in the control device 30.

The master control unit 31 is operated in the first control mode when it is determined that the 3D glasses 13 are positioned in the range stored as the initial position information. In addition, the master control unit 31 is operated in the second control mode when it is determined that the 3D glasses 13 depart from the range stored as the position information. As described above, the master control unit 31 mutually shifts the operation modes. In addition, even in the case of the modified example, when the shift from the second control mode to the first control mode is performed, input of the approval signal by the operator Op using the switch 5 is needed.

Further, the index unit 21A may include any one of the light source 22B and the light source 22C.

Tenth Modified Example

Figure 20:
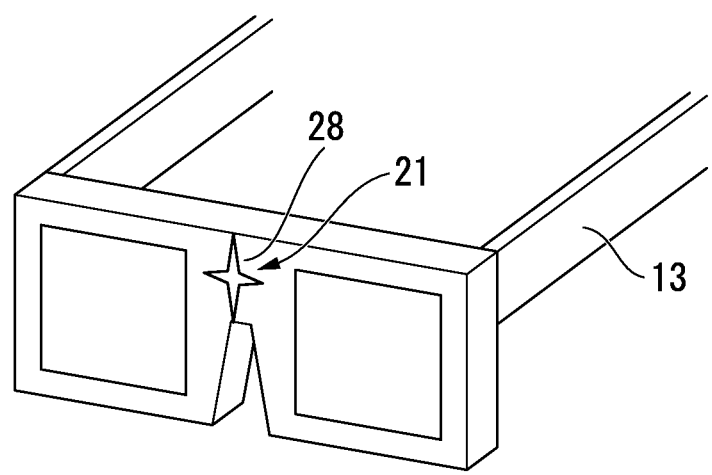
FIG. 20 is a perspective view showing a configuration of 3D glasses of a manipulator system of a tenth modified example of the first embodiment of the present invention.

Next, a tenth modified example of the above-mentioned first embodiment will be described. FIG. 20 is a perspective view showing a configuration of 3D glasses of a manipulator system of the modified example.

In the modified example, the index unit 21 includes an indicator member 28 having a predetermined color or a predetermined shape, and does not include the light source 22. In addition, the detection unit 23 includes the same imaging unit 27 as the above-mentioned eighth modified example, and is configured to acquire an image including the indicator member 28.

Further, the master control unit 31 sets the same range A as the eighth modified example on the image photographed by the imaging unit 27. Furthermore, the master control unit 31 recognizes an area having the predetermined color or the predetermined shape in the image photographed by the imaging unit 27 as the index unit 21 through image treatment.

Even in the modified example, similar to the eighth modified example, when the position of the indicator member 28 is moved from the inside of the range A to the outside, the operation mode of the master control unit 31 is shifted from the first control mode to the second control mode, and when the position of the indicator member 28 is returned to the inside of the range A, a shift from the second control mode to the first control mode is performed via input of the approval signal by the operator Op using the switch 5.

In the case of the modified example, since the indicator member 28 is not an electronic part, the indicator member can be manufactured at a low cost.

In addition, when a display enabling a stereoscopic image with the naked eye is used, an indicator member 28 may be attached to a head mount member instead of the 3D glasses 13. In addition, the indicator member 28 may be attached to a cap or a mask used in surgery. The indicator member 28 in this case may be, for example, a piece of stitchwork, a sticker, or the like.

Eleventh Modified Example

Figure 21:
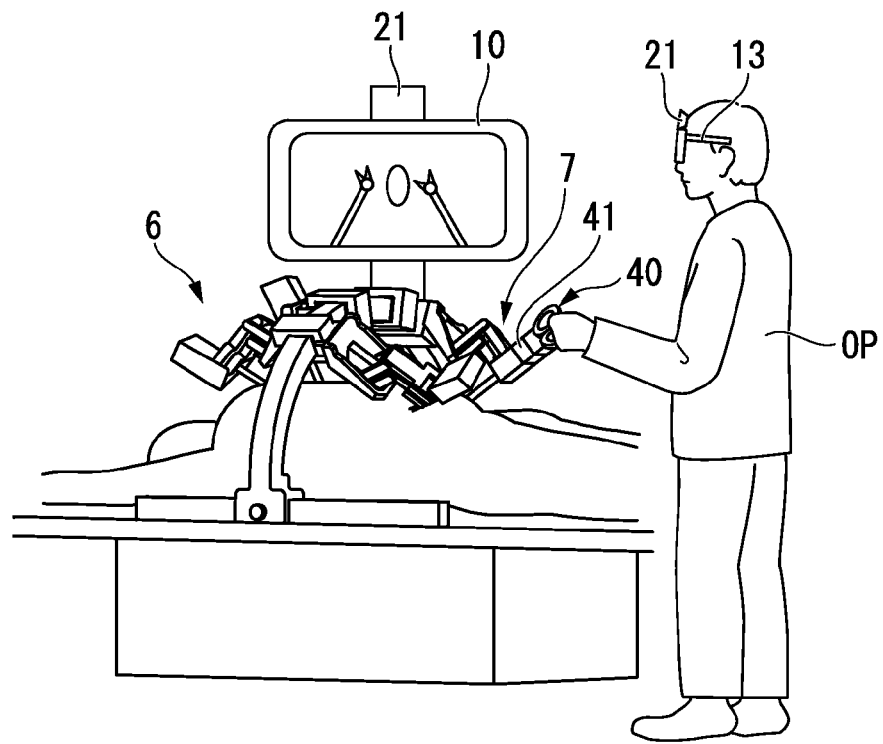
FIG. 21 is a schematic view showing a configuration of a manipulator system of an eleventh modified example of the first embodiment of the present invention.

Next, an eleventh modified example of the above-mentioned first embodiment will be described. FIG. 21 is a schematic view showing a configuration of a manipulator system of the modified example.

The manipulator system of the modified example is a master slave system in which the operator Op performs the treatment with a manual surgical instrument 40 attached to the slave arm 7. The manual surgical instrument 40 may be forceps or a stapler for laparoscopic surgery, an energy treatment tool, and so on. A force measuring instrument 41 configured to measure a force of the operator Op is attached to the slave arm 7, and is controlled such that the slave arm 7 is moved in response to a moving direction of hands of the operator Op.

In the case of the configuration of the modified example, the master control unit 31 controls the slave manipulator 6 to stop with respect to the input of the operator Op in the second control mode. That is, when the operator Op does not look at the display device 10, even when the operator Op intends to move the manual surgical instrument 40, the slave arm 7 is controlled to be stopped and not move. While an input method and a configuration of the master are different from those of the first embodiment, basically, the modified example can be realized through the same method as the master slave system described in the first embodiment (see FIG. 1) and the same effect of the invention can be obtained.

Twelfth Modified Example

Figure 22:
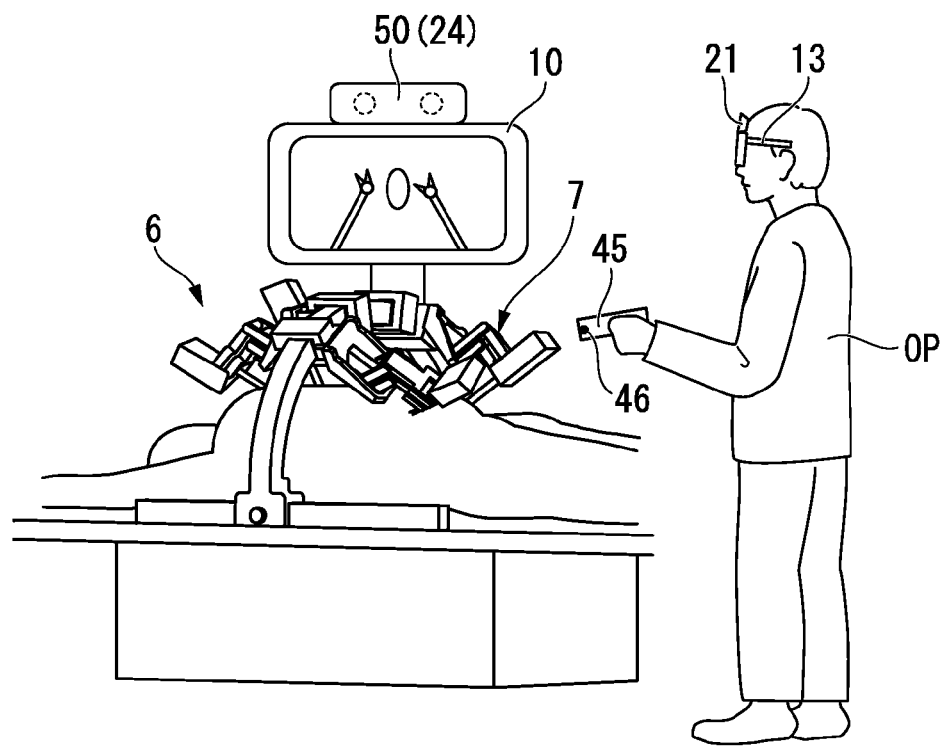
FIG. 22 is a schematic view showing a configuration of a manipulator system of a twelfth modified example of the first embodiment of the present invention.

Next, a twelfth modified example of the above-mentioned first embodiment will be described. FIG. 22 is a schematic view showing a configuration of a manipulator system of the modified example.

In the configuration of the modified example, the operator Op performs the treatment using a master grip 45 in which position/orientation information is obtained by a position sensor 50. In the modified example, the position sensor 50 is a two-lens type imaging sensor. An index 46 detected by the position sensor 50 is attached to the master grip 45. As the position sensor 50 detects the index 46, position and orientation information of the master grip 45 is obtained.

In the case of the configuration of the modified example, the operator Op manipulates the master grip 45, instead of the master arm 3 described in the first embodiment, and performs manipulation input to the slave arm 7, etc. The position sensor 50 obtains the position and orientation information of the master grip 45.

In addition, similar to the eighth modified example, another index may be attached to the head of the operator, and the position of the index may be detected by the position sensor 50 (an imaging unit). In the modified example, the same detection device as described in the above-mentioned eighth modified example can be applied.

While the embodiment of the present invention has been described with reference to the accompanying drawings, a specific configuration is not limited to the embodiment, and includes design change, etc. without departing from the scope of the present invention.

For example, the display device 10 described in the first embodiment may be the display device 10 on which a two-dimensional image is displayed, rather than the stereoscopic image. In this case, there is no need to use the 3D glasses 13.

In addition, the endoscope device 100 having the image capturing unit 101 described in the first embodiment may be held by another holding apparatus, rather than being installed at the slave manipulator 6. Further, an assistant, etc. may hold the endoscope device 100. That is, the image capturing unit 101 is not limited to being installed at the slave manipulator 6.

Furthermore, the second control mode described in the first embodiment may be an operation mode in which the slave manipulator 6 is operated at an operation speed lower than that of the first control mode.

In addition, the second control mode described in the first embodiment may be an operation mode in which only positions of the endoscope device 100, the surgical instrument 110, and the slave arm 7 are fixed, and directions of distal ends of the endoscope device 100, the surgical instrument 110, and the slave arm 7 follow movement of the master arm 3.

Further, in the first embodiment, while the first control mode and the second control mode have been exemplarily described as the operation modes of the master control unit 31, the first control mode and the second control mode may be operation modes of the slave control unit 32. That is, the detection device 20 may be connected to the slave control unit 32 and the slave control unit may be configured such that presence or contents of the driving signal output from the slave control unit 32 are varied based on a result detected by the detection device 20.

Furthermore, the master control unit 31 and the slave control unit 32 may be integrally formed with each other.

In addition, when the manipulator system 1 is in the second control mode, the manipulator system may be configured such that various kinds of medical information are displayed on the display panel 12, instead of the image of the object to be treated. The various kinds of medical information include identification information of patients, results of inspection performed before or during surgery, and so on.

Further, the control device 30 described in the first embodiment may be a general purpose computer. In this case, the master control unit 31 and the slave control unit 32 may be a program operated using a general purpose processor.

Furthermore, components shown in the first embodiment and the modified examples may be appropriately assembled.

While preferred embodiments of the present invention have been described and illustrated above, it should be understood that these are exemplary of the present invention and are not to be considered as limiting. Additions, omissions, substitutions, and other modifications can be made without departing from the spirit or scope of the present invention. Accordingly, the present invention is not to be considered as being limited by the foregoing description, and is only limited by the scope of the appended claims.

What is claimed is:

1. A manipulator system comprising:

a master manipulator configured to send an input command based on manipulation by an operator;

a slave manipulator configured to operate in accordance with the input command;

an image capturing unit configured to acquire an image of an object;

a display device placed in front of the operator and configured to display the image acquired by the image capturing unit;

a detection device configured to detect a direction of an operator's face with respect to the display device; and a control unit configured to determine whether the direction of the operator's face is within a predetermined angle with respect to the display device based on a detection result in the detection device, and to shift an operation mode of the slave manipulator between a predetermined first control mode and a second control mode in which an operation is limited more than in the first control mode based on a determination result;

wherein the detection device comprises:
an index unit that is configured to be mountable on the operator to be moved along with the operator's face; and
a detection unit positioned with respect to the display device and configured to detect the index unit within a predetermined range, and
wherein the control unit operates the slave manipulator in the second control mode when the index unit is not detected within the predetermined range in the detection unit, the control unit shifts to an input standby mode of an approval signal by the operator to perform a shift from the second control mode to the first control mode when a state in which the index unit is not detected within the predetermined range is changed into a state in which the index unit is detected within the predetermined range, and the control unit shifts from the second control mode to the first control mode when the approval signal is input.

2. The manipulator system according to claim 1, wherein the second control mode is a mode in which the slave manipulator is continuously stopped.

3. The manipulator system according to claim 1, wherein the detection device detects a variation of the direction of the operator's face in a horizontal direction in a state in which the display device is placed in front of the operator; and
the control unit shifts to the second control mode when the detection device detects that the direction of the operator's face is varied more than the predetermined angle to the horizontal direction.

4. The manipulator system according to claim 1, wherein the control unit sends a message to prompt the operator to move the operator's face or the display device such that the direction of the operator's face is within a range of the predetermined angle with respect to the display device by using device which is capable of being recognized by the operator, when the control unit determines that the direction of the operator's face deviates from the range of the predetermined angle with respect to the display device.

5. The manipulator system according to claim 1, wherein the control unit sends a message to show a moving direction of the operator's face or a moving direction of the display device such that the direction of the operator's face is within a range of the predetermined angle with respect to the display device by using device which is capable of being recognized by the operator, when the control unit determines that the direction of the operator's face deviates from the range of the predetermined angle with respect to the display device.

6. The manipulator system according to claim 4, wherein the control unit displays the message on the display device.

7. The manipulator system according to claim 1, wherein the display device is provided with a movable mechanism configured to movably support the display device, and
the control unit moves the display device by using the movable mechanism such that the direction of the operator's face is within a range of the predetermined angle with respect to the display device, when the control unit determines that the direction of the operator's face deviates from the range of the predetermined angle with respect to the display device.

8. The manipulator system according to claim 1, wherein the second control mode is a mode in which the slave manipulator is operated at an operation speed lower than the first control mode.

9. The manipulator system according to claim 1, wherein the display device displays two images on the same display surface based on binocular disparity, and
a portion of the detection device is installed at 3D glasses configured to be mountable on the operator and configured to form a stereoscopic image based on the two images.

10. The manipulator system according to claim 9, wherein the detection device detects a distance and a direction of the 3D glasses with respect to the display device, and
the control unit has initial position information showing a range of the distance and direction in which the stereoscopic image is capable of being optimally observed among the distance and the direction, the control unit shifts to the first control mode based on the initial position information, when the distance and the direction of the 3D glasses detected by the detection device are within the range.

11. The manipulator system according to claim 1, wherein the control unit performs a shift from the second control mode to the first control mode without input of the approval signal when the direction of the operator's face is within the range of the predetermined angle with respect to the display device within a predetermined time from when the first control mode is shifted to the second control mode.

12. The manipulator system according to claim 1, wherein the control unit performs a shift from the second control mode to the first control mode without input of the approval signal when the direction of the operator's face is within the range of the predetermined angle with respect to the display device while an operation amount of the master manipulator from when the shift from the first control mode to the second control mode is performed is within a predetermined operation amount.

13. The manipulator system according to claim 1, wherein the index unit has a predetermined color or a predetermined shape,
the detection unit includes an imaging unit configured to acquire an image including the index unit, and
the control unit sets the predetermined range on the image and recognizes an area having the predetermined color or the predetermined shape in the image as the index unit.

14. The manipulator system according to claim 1, wherein the index unit includes a plurality of index elements spaced apart from each other in at least one of a horizontal direction or a vertical direction of the operator wearing the index unit, and
the detection unit detects the direction of the index unit based on a result in which positions of the plurality of index elements are detected.

* * * * *